US011266630B2

(12) United States Patent
Chen et al.

(10) Patent No.: US 11,266,630 B2
(45) Date of Patent: Mar. 8, 2022

(54) ORAL PREPARATION OF GLUCOKINASE ACTIVATOR AND PREPARATION METHOD THEREFOR

(71) Applicant: Hua Medicine (Shanghai) Ltd., Shanghai (CN)

(72) Inventors: Li Chen, Shanghai (CN); Yongguo Li, Shanghai (CN); Gaosen Wang, Shanghai (CN)

(73) Assignee: Hua Medicine (Shanghai) Ltd., Shanghai (CN)

( * ) Notice: Subject to any disclaimer, the term of this patent is extended or adjusted under 35 U.S.C. 154(b) by 0 days.

(21) Appl. No.: 16/470,291

(22) PCT Filed: Dec. 14, 2017

(86) PCT No.: PCT/CN2017/116209
§ 371 (c)(1),
(2) Date: Jun. 17, 2019

(87) PCT Pub. No.: WO2018/108128
PCT Pub. Date: Jun. 21, 2018

(65) Prior Publication Data
US 2019/0328713 A1 Oct. 31, 2019

(30) Foreign Application Priority Data
Dec. 15, 2016 (CN) .......................... 201611162346.7

(51) Int. Cl.
A61K 31/426 (2006.01)
A61K 31/4155 (2006.01)
A61K 9/20 (2006.01)
A61K 31/427 (2006.01)
A61K 31/437 (2006.01)
A61K 31/4439 (2006.01)
A61K 31/444 (2006.01)
A61K 31/497 (2006.01)

(52) U.S. Cl.
CPC ........ A61K 31/4155 (2013.01); A61K 9/2013 (2013.01); A61K 9/2031 (2013.01); A61K 9/2054 (2013.01); A61K 31/426 (2013.01); A61K 31/427 (2013.01); A61K 31/437 (2013.01); A61K 31/444 (2013.01); A61K 31/4439 (2013.01); A61K 31/497 (2013.01)

(58) Field of Classification Search
None
See application file for complete search history.

(56) References Cited

U.S. PATENT DOCUMENTS

| 5,985,326 A * | 11/1999 | Butler ................. A61K 31/437 424/484 |
| 7,741,327 B2 | 6/2010 | Berthel et al. |
| 2006/0083784 A1 | 4/2006 | Ignatious et al. |
| 2008/0107725 A1 * | 5/2008 | Albano ................. A61K 47/32 424/451 |
| 2009/0264445 A1 * | 10/2009 | Berthel ................. A61P 43/00 514/255.05 |
| 2014/0212487 A1 * | 7/2014 | Mogalian ............. A61K 31/501 424/465 |
| 2014/0336267 A1 | 11/2014 | Tokuda et al. |
| 2016/0015638 A1 | 1/2016 | Mo et al. |
| 2019/0046645 A1 | 2/2019 | Benjamin et al. |

FOREIGN PATENT DOCUMENTS

| CN | 102007118 A | 4/2011 |
| CN | 104739848 A | 7/2015 |
| CN | 105050585 A | 11/2015 |
| CN | 106456539 A | 2/2017 |
| CN | 106474480 A | 3/2017 |
| JP | 2008531534 A | 8/2008 |
| JP | 2010505901 A | 2/2010 |
| JP | 2011517692 A | 6/2011 |
| JP | 2016510741 A | 4/2016 |
| JP | 2016513625 A | 5/2016 |
| WO | 2008/043701 A1 | 4/2008 |
| WO | 2009127546 A1 | 10/2009 |

(Continued)

OTHER PUBLICATIONS

Chen et al. (Abstract 134-LB; p. LB35 in ADA Late Breaking Abstracts, Jun. 2014) (Year: 2014).*
ChemDraw (Chemical Properties Window) utilized Dec. 15, 2020, available since at least 2014. (Year: 2014).*
Jadhav et al (Research J Pharm and Tech 5:190-197, 2012) (Year: 2012).*
Office Action dated Jun. 16, 2020 issued in counterpart application, JP 2019-553613; 7 pgs.
Yu et al., "Preparation of Metformin enteric sustained release microcapsules by spray drying," China Academic Journal Electronic Publishing House (2011); 2692):115-117.
Xu et al., "Saftery, tolerability, pharmacokinetics, and pharmacodynamics of novel GK activator HMS5552: results from a first-in human single ascending dose study," Drug, Design, Development and Therapy (2016); 10:1-8.

(Continued)

Primary Examiner — Craig D Ricci
(74) Attorney, Agent, or Firm — Fox Rothschild LLP

(57) ABSTRACT

Disclosed is a solid dispersion and a preparation method therefor. The solid dispersion contains a glucokinase activator, an isotopic label thereof, or a medicinal salt thereof and a polymer support. Further disclosed is a solid dispersion composition containing the solid dispersion and an excipient. Also disclosed is an oral preparation of the glucokinase activator, containing the solid dispersion or the solid dispersion composition. Also disclosed is a tablet and a capsule of the glucokinase activator and a preparation method therefor. In addition, also disclosed is the uses of the solid dispersion, the solid dispersion composition and the oral preparations comprising the tablet and the capsule, which can be used for treating and/or preventing selected diseases or medical conditions and especially one or more diseases selected from type I diabetes mellitus, type II diabetes mellitus, impaired glucose tolerance, impaired fasting glucose and hyperglycemia.

34 Claims, 7 Drawing Sheets

(56) References Cited

FOREIGN PATENT DOCUMENTS

| WO | 2014102164 A1 | 7/2014 |
|---|---|---|
| WO | 2014137797 A2 | 9/2014 |
| WO | 2014137799 A1 | 9/2014 |
| WO | 2015103230 A9 | 10/2015 |

OTHER PUBLICATIONS

The First Office Action issued by the Korean Patent Office in the corresponding Korean application No. 10-2019-7020462. The Office Action dated Oct. 13, 2020.
The Hearing Notice issued by the Indian Patent Office in the corresponding Indian application No. 201927027139. The Office Action dated Nov. 18, 2020.
Saudi Pharmaceutical Journal (2015) 23, 352-365, Revealing facts behind spray dried solid dispersion technology used for solubility enhancement.
Office Action (with English translation) from related Chinese Application No. 201910104895.6, dated Apr. 6, 2021; 13 pgs.
Office Action (with English translation) from related Taiwanese Application No. 106144500, dated Apr. 28, 2021; 15 pgs.
Jadhav et al., "Solid Dispersion Solubility Enhancement for Poorly Water Soluble Drug," Research J. Pharm. and Tech. (2012); 5(2): 190-197.
First Office Action from related Brazilian application No. 112019011098-4, dated Sep. 8, 2021; 5 pgs.

* cited by examiner

ORAL PREPARATION OF GLUCOKINASE ACTIVATOR AND PREPARATION METHOD THEREFOR

CROSS REFERENCE TO RELATED APPLICATIONS

The present application is a national application of PCT/CN2017/116209 filed on Dec. 14, 2017, which claims the priority of the Chinese Patent Application No. 201611162346.7 filed on Dec. 15, 2016. The Chinese Patent Application No. 201611162346.7 is incorporated herein by reference as part of the disclosure of the present application.

TECHNICAL FIELD OF THE INVENTION

The disclosure relates to the the oral formulation of the glucokinase activator, more particularly, the disclosure relates to the oral modified release formulation of the glucokinase activator, the preparation method thereof and the use thereof for treating specific diseases.

In further embodiment, the disclosure relates to the regulation of release behavior of the oral formulation of the glucokinase activator in human body, so as to achieve the purpose of exerting better efficacy and reduced side effects. The modified release of the the oral formulation of the glucokinase activator disclosed herein in human body matches the pharmacokinetics (PK) with the pharmacodynamics (PD) (PK/PD Correlation) during disease treatment. The modified release includes the modified release of the oral formulation of the glucokinase activator in gastrointestinal tract of human body and the rapid release of the oral formulation of the glucokinase activator in small intestine of human body. The disclosure relates to the solid dispersion of the glucokinase activator used in the oral formulation of the glucokinase activator, the composition of the solid dispersion of the glucokinase activator and the preparation method thereof, as well as the types of the polymer carriers. The disclosure further relates to the preparation method of the oral formulation of the glucokinase activator.

The disclosure relates to the use of the oral formulation of the glucokinase activator, solid dispersion and solid dispersion composition, for treating and/or preventing selected diseases and medical disorders, particularly one or more diseases selected from the group consisting of type I diabetes, type II diabetes, impaired glucose tolerance, impaired fasting glucose and hyperglycemia. In addition, the disclosure relates to a method of treating and/or preventing said diseases and medical disorders, comprising administering a therapeutically effective amount of the oral formulations disclosed herein, including the oral modified release formulation, to a patient in need thereof.

BACKGROUND OF THE INVENTION

Type II Diabetes and Glucokinase Activators

Diabetes mellitus has become a prevalent disease worldwide, with 415 million patients over the world, and 110 million patients in China (International Diabetes Federation, Diabetes Atlas, 2015). Type II diabetes, i.e., non-insulin dependent diabetes mellitus (NIDDM), accounts for more than 90% of the patients with diabetes. This is a hyperglycemic, chronic, metabolic dysfunction resulting from an imbalance of blood glucose homeostasis in human body caused by insulin secretion disorder and insulin resistance. The blood glucose balance of the human body is mainly coordinated by two hormones that control blood glucose, including insulin and glucagon. GLP-1 (glucagon-like peptide-1) is involved in the regulation of insulin secretion, and is also a molecular factor and a therapeutic drug for diabetes that plays an important role in the blood glucose balance in human body. Insulin and GLP-1 analogues have become important drugs for the treatment of diabetes.

Glucokinase (GK) is hexokinase isoform IV (Colowick, S. P., The hexokinase, in The Enzymes, $3^{rd}$ ed., Boyer, P. D., Ed., Vol. 9, Academic Press, New York, 1973, chap. 1), and the change of its activity is regulated by the glucose concentration. It can sense the change of glucose concentration in the body, regulate the secretion of hormones of glucose metabolism, including insulin, glucagon and GLP-1, and meanwhile rapidly convert the glucose uptaken after meal into hepatic glycogen in liver to maintain blood sugar balance. Glucokinase therefore plays a central role in stabilizing the blood glucose balance in human body. Maturity-onset type II diabetes (MODY-2) is a functional impairment caused by functional mutation of the glucokinase gene, making the mutated glucokinase to be activated with higher concentrations of glucose. This impairs the glucose-stimulated insulin secretion function in islets of patients, and reduces the ability of hepatic glycogen synthesis, and finally resulting in hyperglycemia. Studies have shown that the expression and function of glucokinase in the liver and islets of patients with type II diabetes are significantly lower than those in healthy population. Therefore, up-regulating the activity of glucokinase in diabetic patients is beneficial for the treatment of hyperglycemia and type II diabetes caused by impaired glucose tolerance.

Glucokinase is mainly distributed in the liver, which rapidly converts glucose into hepatic glycogen for storage in response to elevated blood glucose, and meanwhile lowering the glucose level in the blood. Glucokinase is expressed in endocrine cells, alpha cells and beta cells of islets, and L cells in the gut, and is a major functional protein that regulates the secretion of glucagon, insulin, and GLP-1 stimulated by glucose. Glucokinase activators are developed according to the characteristics of this target, which are capable of systematically stabilizing the blood glucose level in the body by improving the sensitivity of alpha cells, beta cells and L cells to the changes of glucose concentration; improving the secretion functionality of insulin, glucagon and GLP-1 regulated by glucose; regulating hepatic glucose export to promote hepatic glycogen synthesis and other synergistic mechanisms. Glucokinase activators have become one of the most popular targets for the development of new drugs for type II diabetes (type 2 diabetes) (Matschinsky F M, Nat Rev Drug Discov. 2009, 8(5): 399-416). Decreased expression and function of glucokinase causes early-phase insulin secretion disorders and hepatic glycogen generation disorders. Drugs for diabetes in current clinical use, including insulin, cannot solve this problem. There is a clinical need to be met in the field of diabetes. (S)-2-[4-(2-chloro-phenoxy)-2-oxo-2,5-dihydro-pyrrol-1-yl]-4-methyl-pentanoic acid [1-((R)-2,3-dihydroxy-propyl)-1H-pyrazol-3-yl]-amide (hereinafter referred to as HMS5552) is currently the most promising drug for diabetes treatment that may meet the above mentioned clinical needs. Oral hypoglycemic drugs are the first choice for clinical use because of their ease of administration and portability as well as safety. The novel drugs of the glucokinase activator are also suitable for oral formulations, especially oral solid formulations. Oral formulations can be categorized into oral solid formulations and oral liquid formulations. The oral solid formulations include tablets, capsules, granules, powders, lozenges, pills, and the like.

SUMMARY OF THE INVENTION

In combination of the characteristics of blood glucose fluctuations in diabetic patients throughout the day, including regulation of fasting and postprandial blood glucose, the target and mechanism of glucokinase, its distribution in human body, and function of blood glucose regulating sensor, etc., the inventors design and provide an oral formulation suitable for glucokinase activators, in which the pharmacokinetics (PK) and pharmacodynamics (PD) are matched (PK/PD Correlation).

Since the major targeting organs of the glucokinase distribute in the liver, pancreas and intestine, the present disclosure contemplates to achieve a timely or simultaneous activation of the targeting each target organ by the glucokinase activator, thereby ensuring the efficacy and safety of the drug.

The oral formulation of the glucokinase activator of the present disclosure is designed to: 1) achieve an appropriately reduced release in stomach, and a rapid release in small intestine; 2) utilize the intestinal pH environment to regulate the release and absorption of the glucokinase activator. The rapid release of the glucokinase activator in human small intestine is beneficial to the timely or simultaneous arrival of drugs in the gut, islets and liver target organs, achieving a multi-point target, synergistic hypoglycemic clinical advantage, and exhibiting a better therapeutic effect and reduced toxic or side effects.

Accordingly, one object of the disclosure is to provide an oral formulation of the glucokinase activator, in particular an oral, modified release formulation, and the preparation method thereof, wherein the formulation comprises a solid dispersion of the glucokinase activator and excipients.

Another object of the disclosure is a solid dispersion comprising the glucokinase activator, including the composition of the solid dispersion, the preparation method, and the types of polymer carriers.

Another object of the disclosure is a solid dispersion composition comprising the glucokinase activator, including the solid dispersion of the disclosure and excipients.

A further object of the disclosure is to provide a method and use for the treatment and/or prevention of one or more diseases selected from the group consisting of type I diabetes, type II diabetes, impaired glucose tolerance, impaired fasting glucose and hyperglycemia, comprising using the oral formulation of the glucokinase activator, including the oral, modified release formulation, the solid dispersion or the solid dispersion composition.

Other objects of the disclosure will be apparent to those skilled in the art from the description and examples.

Definition

As used herein, the term "about" means ±5% of the specified value.

Weight % (wt %) means the weight percent relative to the total weight of the solid dispersion.

Solid dispersion (SD) means a solid dispersion system generated by dispersing one or more pharmaceutical active ingredients into inactive adjuvants or carriers. In the solid dispersion, the drugs in the carriers are in the form of molecule, colloid, microcrystalline, amorphous or the mixture thereof, and the like (Naveen Dutt Dixit, Suneel Kumar Niranjan. A REVIEW: SOLID DISPERSION. WORLD JOURNAL OF PHARMACY AND PHARMACEUTICAL SCIENCES, 2014, Vol 3, Issue 9: 238-257). Depending on the distribution of the drug molecules in the solid carriers, the type of solid dispersion includes: a co-melting mixture; a solid solution, including a continuous solid solution and a discontinuous solid solution; a substitutional crystallization solution; a gap-type crystallization solution; an amorphous solid solution; glassy solution, and glassy suspension, etc (Shrawan Baghel, Helen Cathcart, Niall J. O'Reilly. Polymeric Amorphous Solid Dispersions: A Review of Amorphization, Crystallization, Stabilization, Solid-State Characterization, and Aqueous Solubilization of Biopharmaceutical Classification System Class II Drugs. Journal of Pharmaceutical Sciences 105 (2016) 2527-2544). Solid dispersion can be prepared by solid hot melt extrusion, liquid spray drying, and melt-solvent methods, and the like (T. Vasconcelos, B. Sarmento, P. Costa, Solid dispersions as strategy to improve oral bioavailability of poor water soluble drugs, Drug Disc. Today 12 (2007) 1068-1075).

EUDRAGIT is the trade name of a synthetic pharmaceutical adjuvant, which includes methacrylic acid copolymer and methacrylate copolymer, commonly known as polyacrylic resins. Polyacrylic resins are classified into different models depending on their composition, ratio and degree of polymerization. Among them, Eudragit E is a polymer of dimethylaminoethyl methacrylate and methacrylate; Eudragit L is a polymer of methacrylic acid and methyl methacrylate, wherein free carboxyl:ester=1:1, Eudragit S is a polymer of methacrylic acid and methyl methacrylate, wherein free carboxyl:ester=1:2.

The terms "effective amount" or "therapeutically effective amount" refer to an amount of the agent sufficient to provide the desired biological result. The biological result may be a reduction and/or alleviation of the signs, symptoms, or causes of a disease, or any other desired alteration of a biological system. For example, an "effective amount" for therapeutic use is the necessary amount of the composition comprising a compound as disclosed herein for providing a clinically significant decrease in a disease. An appropriate "effective" amount in any individual embodiment may be determined by one of ordinary skill in the art using routine experimentation. Thus, the expression "effective amount" generally refers to the quantity for which the active substance has therapeutic effects.

As used herein, the terms "treat" or "treatment" are synonymous with the term "prevent" and are meant to indicate a postponement of development of diseases, preventing the development of diseases, and/or reducing severity of such symptoms that will or are expected to develop. Thus, these terms include ameliorating existing disease symptoms, preventing additional symptoms, ameliorating or preventing the underlying metabolic causes of symptoms, inhibiting the disorder or disease, e.g., preventing the development of the disorder or disease, relieving the disorder or disease, causing a regression of the disorder or disease, relieving a condition caused by the disease or disorder, or stopping the symptoms of the disease or disorder.

By "pharmaceutically acceptable" or "pharmacologically acceptable", it is meant a material which is not biologically or otherwise undesirable, i.e., the material may be administered to an individual without causing a minimum of undesirable biological effects or interacting in a deleterious manner with any of the components of the composition in which it is contained.

As used herein, the term "subject" encompasses mammals and non-mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the present disclosure, the mammal is a human.

The compounds that can be used as the active ingredient of the present solid dispersion of the glucokinase activator can form salts which are also within the scope of this disclosure. Reference to a compound disclosed herein is understood to include reference to salts thereof, unless otherwise indicated. The term "salt(s)", as used herein, denotes acidic salts formed with inorganic and/or organic acids, as well as basic salts formed with inorganic and/or organic bases. In addition, when a compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds may be formed, for example, by reacting the compound disclosed herein with an amount of acid or base, such as an equivalent amount, in a medium such as a medium from which the salt precipitates or in an aqueous medium (lyophilization after reaction).

Various compound and the salts, solvates, esters and prodrugs thereof, and their polymorphs thereof are intended to be included in the disclosure.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, the term "alkyl", alone or in combination with other groups, refers to a branched or straight monovalent saturated aliphatic hydrocarbon radical of one to twenty carbon atoms, preferably one to sixteen carbon atoms, more preferably one to ten carbon atoms.

The term "lower alkyl", alone or in combination with other groups, refers to a branched or straight alkyl radical of one to nine carbon atoms, preferably one to six carbon atoms. This term is further exemplified by radicals such as methyl, ethyl, n-propyl, isopropyl, n-butyl, s-butyl, isobutyl, t-butyl, n-pentyl, 1-ethylpropyl, 3-methylbutyl, n-hexyl, 2-ethylbutyl and the like. Especially preferred are methyl and ethyl.

As used herein, the term "lower alkenyl", alone or in combination with other groups, refers to a straight or branched hydrocarbon group of one to nine carbon atoms, preferably one to six carbon atoms having an olefinic bond. Preferred lower alkenyl is 2-propenyl.

The term "cycloalkyl" refers to a monovalent mono- or polycarbocyclic radical of three to ten, preferably three to seven carbon atoms and more preferably four to six carbon atoms. This term is further exemplified by radicals such as cyclopropyl, cyclobutyl, cyclopentyl, cyclohexyl, cycloheptyl, bornyl, adamantyl, bicyclo[2.2.1]heptyl, indenyl and the like. In a preferred embodiment, "cycloalkyl" means cyclobutyl, cyclopentyl or cyclohexyl.

The term "heterocyclyl" denotes a mono- or polycyclic saturated ring, wherein one, two or three of the carbon ring atoms is replaced by a heteroatom such as N, O or S. Examples of heterocyclyl groups include, but are not limited to, morpholinyl, thiomorpholinyl, piperazinyl, piperidinyl, pyrrolidinyl, tetrahydropyranyl, tetrahydrofuranyl, 1,3-dioxanyl and the like. Preferred heterocyclyl groups are pyrrolidinyl, piperidinyl, morpholinyl or tetrahydropyranyl. The heterocyclyl groups may be unsubstituted or substituted and attachment may be through their carbon frame or through their heteroatom(s) where appropriate, with the understanding that said substituents are not, in turn, further substituted unless indicated otherwise in the Examples or claims below.

The term "aryl" refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphtalene, 1,2-dihydronaphtalene, indanyl, 1H-indenyl and the like. Preferred aryl groups are phenyl or naphthyl, with phenyl being especially preferred.

The term "heteroaryl" refers to an aromatic mono- or polycyclic radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group. Preferred heteroaryl rings are selected from the group consisting of pyrrolyl, pyrazolyl, imidazolyl, triazolyl, tetrazolyl, oxazolyl, oxadiazolyl, isoxazolyl, thiadiazolyl, thiazolyl, furanyl, thienyl, pyranyl, pyridyl, pyrazinyl, pyrimidinyl, pyridazinyl, indolyl, isoindolyl, indazolyl, 7-azaindolyl, quinolinyl, isoquinolinyl, cinnolinyl, pyrazolo[1,5-a]pyridyl, imidazo[1,2-a]pyridyl, quinoxalinyl, benzofuranyl, benzoxazinyl, benzothiazolyl, benzotriazolyl, chromenyl, chromanyl, isochromanyl, coumarinyl, isocoumarinyl and benzopyranyl. Preferred heteroaryl groups are selected from the group consisting of 1H-pyrazol-3-yl, thiazol-2-yl, [1,2,4]thiadiazol-5-yl, [1,3,4]thiadiazol-2-yl, pyridyl, pyrazinyl and pyrimidinyl.

The term "heteroaryl," refers to an aromatic mono- or polycyclic radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group.

As used herein, the term "lower alkoxy" means the group R'—O—, wherein R' is lower alkyl and the term "lower alkyl" has the previously given definition. Examples of lower alkoxy groups are methoxy, ethoxy, n-propoxy, isopropoxy, n-butoxy, isobutoxy, sec-butoxy and tert-butoxy, preferably methoxy and ethoxy.

The term "lower alkoxyalkyl" refers to the group —R"—O—R', wherein R' signifies a lower alkyl group as defined herein before and R" represents a lower alkylene group such as methylene, ethylene or propylene. Examples of lower alkoxyalkyl groups are methoxymethyl or 2-methoxy-ethyl.

As used herein, the term "halogen" means a fluorine, chlorine, bromine or iodine radical, preferably a fluorine, chlorine or bromine radical, and more preferably a fluorine or chlorine radical.

The term "lower haloalkyl" refers to lower alkyl groups as defined above wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, trifluoroethyl, 2,2-difluoroethyl, fluoromethyl and chloromethyl, with trifluoromethyl being especially preferred.

The term "carboxyl" means the group —COOH, whereas the term "aminocarbonyl" refers to the group —CO—NH$_2$.

The term "lower alkoxycarbonyl" refers to the group —CO—OR' wherein R' is lower alkyl and the term "lower alkyl" has the previously given definition. Preferred lower alkoxycarbonyl groups are methoxycarbonyl or ethoxycarbonyl.

"lower alkylthioalkyl" refers to the group —R"—S—R', wherein R' is lower alkyl as defined above, and R" represents lower alkylene such as methylene, ethylene and propylene. Instances of lower alkylthioalkyl is methylthiomethyl or 2-methylthio-ethyl.

"Lower alkoxycarbonylamino" refers to a group —NH—CO—OR', wherein R' is lower alkyl.

The term "lower alkenyloxycarbonyl" refers to a group —CO—OR*, wherein R* is a lower alkenyl group. A preferred "lower alkenyloxycarbonyl" group is 2-propen-1-yloxycarbonyl or allyloxycarbonyl.

As used herein, the term "lower alkanoyl" means a group —CO—R' wherein R' is lower alkyl and the term "lower alkyl" has the previously given definition. Preferred lower alkanoyl group is acetyl.

Compounds used as active ingredients have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). The disclosure embraces all of these forms.

The dose of the compound of the present disclosure depends on a number of factors, such as, for example, the manner of administration, the age and the body weight of the patient, and the condition of the patient to be treated, and ultimately will be decided by the attending physician or veterinarian. Such an amount of the active compound as determined by the attending physician or veterinarian is referred to herein, and in the claims, as a "therapeutically effective amount". For example, the dose of the compound of the present disclosure is typically in the range of about 1 to about 1000 mg per day. Preferably, the therapeutically effective amount is in an amount of from about 1 mg to about 500 mg per day.

The preparation methods of solid dispersion include melting method, solvent method, solvent-melting method, spray drying method, freeze drying method, grinding method, and the like. Melting method refers to mixing and melting a drug with a carrier material and rapidly cooling to solid, and then placing the solid at a certain temperature to become a fragile substance, such as a dropping pill. The method is suitable for thermally stable drugs and for carrier materials with low melting point and poorly solubility in an organic solvent, such as PEG, citric acid, sugar, and the like. The solvent method is also called co-precipitation method, which means that the drug and the carrier are co-dissolved in an organic solvent and then the solvent is evaporated, so that the drug and the carrier material are precipitated simultaneously. The solid dispersion of the drug and the carrier material is thus obtained after drying. The method is suitable for the carrier materials which are volatile, thermally unstable, and soluble in organic solvents.

Spray drying is a method in which fluidized technology is applied for drying liquid materials. The basic principle is that the liquid material system (solution, suspension, emulsion, etc.) is atomized by gas in a drying tower (chamber). By contacting with hot air, moisture (solvent) is rapidly vaporized, and finally a dried powder product is obtained. The method can be used directly to dry a solution, a suspension, an emulsion and the like into a powdery or granular product, thereby eliminating the procedures of evaporation and pulverization.

Spray drying method includes pressure spray drying, centrifugal spray drying and airflow spray drying.

(1) Pressure Spray Drying:

① Principle: By using a high-pressure pump, the material is passed through an atomizer (gun) at a pressure of 70 to 200 atmospheres, and the misty particles of 10 to 200 thus obtained are directly contacted with hot air for heat exchange and the drying is completed in a short time.

(2) Centrifugal Spray Drying:

① Principle: The disc which is rotated at a high speed in the horizontal direction provides a centrifugal force for a solution, so to make it flash out at high speed to form a film, a filament or a droplet. Due to the friction, the hindrance and the tear from the air in combination with the tangential acceleration generated by the rotating of the disc and radial acceleration generated by the centrifugal force, the film, filament or droplet moves on the disc at a combined speed, with the trace of a spiral shape. The liquid is dispersed into tiny droplets after being thrown from the disc along the spiral, the droplets then move in the direction of the chopped diameter of the disc at an average speed. Meanwhile, the droplets fall under the action of gravity. Due to the different sizes of the sprayed particles, their flight distances in the air are different. The particles falling at different distances form a cylinder that is symmetric about the center of the shaft.

(3) Airflow Spray Drying:

① Principle: The wet materials enter the dryer through the conveyor with heated natural air, and then intensively mixed. Due to the large heat and mass transfer area, the evaporative drying is achieved in a short time.

Spray drying methods are widely used in the food industry (such as milk powder), pharmaceutical industry (drying of Traditional Chinese Medicine, solid dispersion preparation, particle size reduction, etc.), chemical industry, plastics industry and ceramics production.

BRIEF DESCRIPTIONS OF THE DRAWINGS

Figure 7:
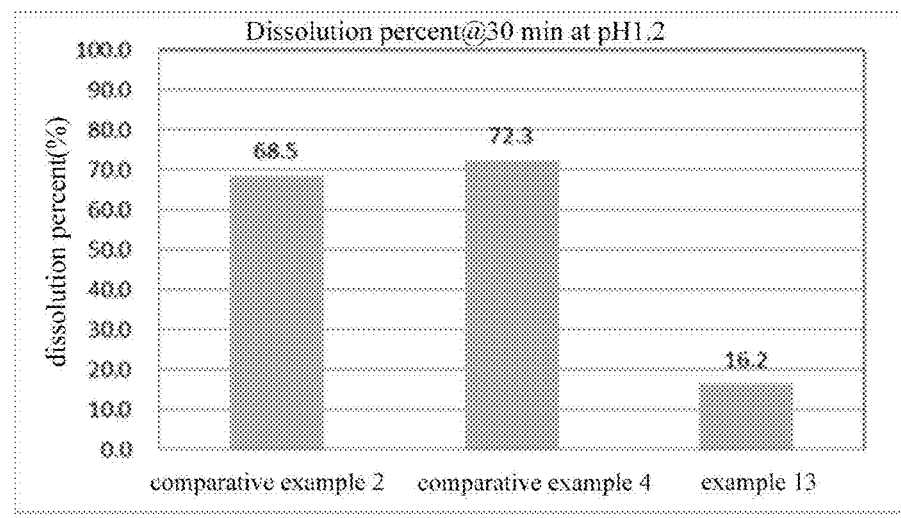

FIG. 7 is a histogram which shows the 30 min dissolution results of the 75 mg tablets prepared in Example 13, comparative example 2 and comparative example 4 at pH 1.2, respectively.

Figure 8:
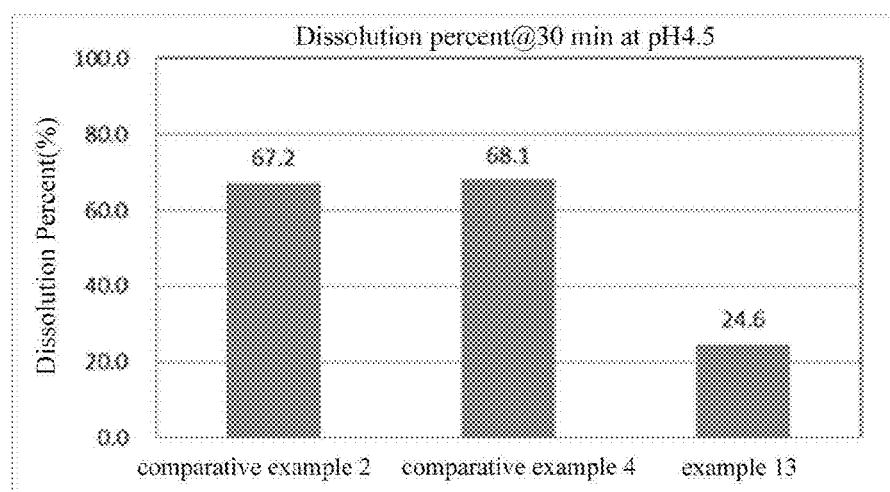

FIG. 8 is a histogram which shows the 30 min dissolution result of the 75 mg tablets prepared in Example 13, comparative example 2 and comparative example 4 at pH 4.5, respectively.

Figure 9:
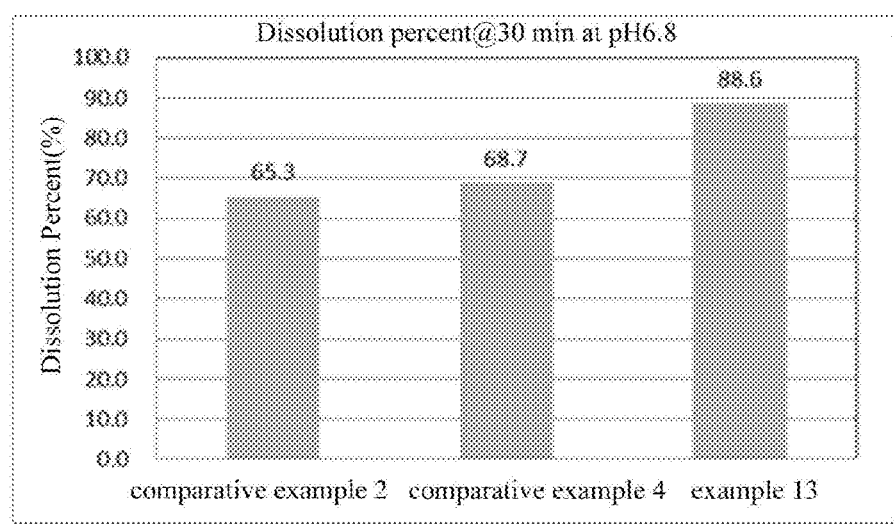

FIG. 9 is a histogram which shows the 30 min dissolution result of the 75 mg tablets prepared in Example 13, comparative example 2 and comparative example 4 at pH pH 6.8, respectively.

EMBODIMENTS OF THE INVENTION

The disclosure relates to the modified release technique of the glucokinase activator. Particularly, the disclosure relates to the design and preparation of the the oral formulation of the glucokinase activator. The oral formulation, preferably an oral, modified release formulation, and further preferably an oral, modified release, solid formulation, is released in a small amount in gastric juice, but rapidly released and gradually absorbed in the intestinal tract, so that the pharmacokinetics (PK) is matched with the pharmacodynamics (PD) (PK/PD Correlation) in human body. The plasma concentration versus time cure (C-t curve) in human body has an inverted U shape.

In one embodiment, the disclosure relates to a solid dispersion, which comprises the glucokinase activator, or isotope labeled analogues thereof or pharmaceutically acceptable salts thereof and polymer carriers.

In one embodiment, the disclosure relates to a solid dispersion, wherein the glucokinase activator is a compound of formula (Ia),

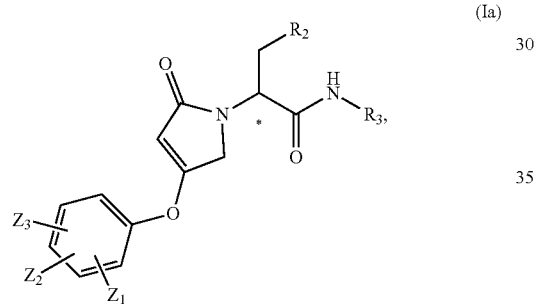

(Ia)

wherein:

$Z_1$, $Z_2$, $Z_3$ independently of each other, are hydrogen, lower alkyl, lower alkenyl, hydroxy, —$NH_2$, halogen, lower alkoxy, —$CF_3$, —$OCF_3$, —$S(CH_3)$, —$S(O_2)CH_3$, —$CH_2$-aryl, heteroaryl, cyano, lower alkanoyl, —O-aryl, —O—$CH_2$-aryl, —$N(CH_3)_2$, cycloalkyl, heterocyclyl, —C(O)-heterocyclyl, or lower alkyl mono- or di-substituted with hydroxy;

$R_2$ is selected from the group consisting of lower alkyl, lower alkyl mono- or di-substituted with hydroxy, lower haloalkyl, lower alkoxyalkyl, lower alkylthioalkyl, lower alkoxy, cycloalkyl, said cycloalkyl being unsubstituted or mono- or di-substituted independently with halogen or lower alkyl, heterocyclyl and aryl, said aryl being unsubstituted or mono- or di-substituted independently with halogen; and $R_3$ is -lower alkyl-carbamoyl or an unsubstituted or substituted heteroaryl connected to the amine group as shown through a ring carbon atom, wherein one of the heteroatoms is nitrogen and it is adjacent to the connecting ring carbon atom, said substituted heteroaryl is substituted at a position other than positions adjacent to said connecting carbon atom independently with a group selected from the group consisting of:

lower alkyl, halogen, lower alkoxycarbonyl, cyano, carboxyl, cycloalkyl, aryl, 2-oxo-oxazolidin-5-ylmethyl, —N(lower alkyl)$_2$, 2,2-dimethyl-[1,3]dioxolan-4-yl, —$CH_2$-dimethyl-[1,3]dioxolane, t-butyl-dimethyl-silanyloxy-ethyl, unsubstituted —$CH_2$-aryl, —$CH_2$-aryl substituted with cyano or alkoxy, heterocyclyl, —$CH_2$-heterocyclyl, -6-($CH_2$)-2,2-dimethyl-[1,3]dioxan-4-yl-acetic acid tert-butyl ester, and lower alkyl mono-, di- or tri-substituted independently with hydroxy, halogen, alkoxy, —N(lower alkyl)$_2$, —$NH_2$, lower alkanoyl, lower alkoxycarbonyl, lower alkenyloxycarbonyl, carboxyl, aminocarbonyl or lower alkoxycarbonylamino, or isotope labeled analogues or pharmaceutically acceptable salts thereof.

In one embodiment, the disclosure relates to a solid dispersion, wherein the glucokinase activator is selected from the following compounds, or isotope labeled analogues or pharmaceutically acceptable salts thereof:

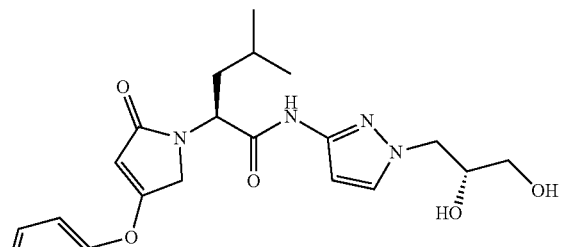

HMS5552

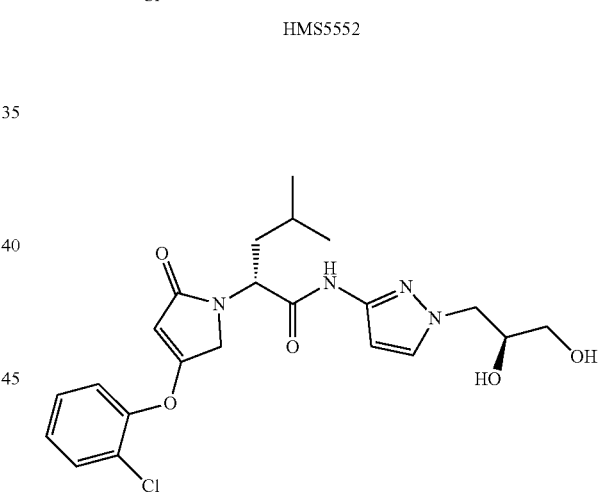

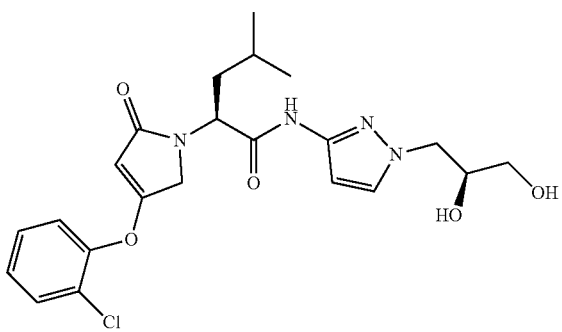

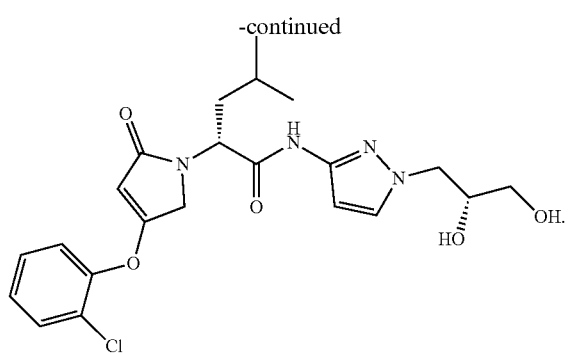
In one embodiment, the disclosure relates to a solid dispersion, wherein the glucokinase activator is the compound HMS5552, or isotope labeled analogues or pharmaceutically acceptable salts thereof:
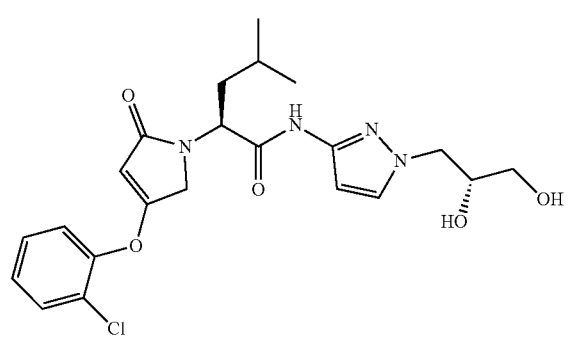
HMS5552
In one embodiment, the disclosure relates to a solid dispersion, wherein the glucokinase activator is selected from the group consisting of:
1
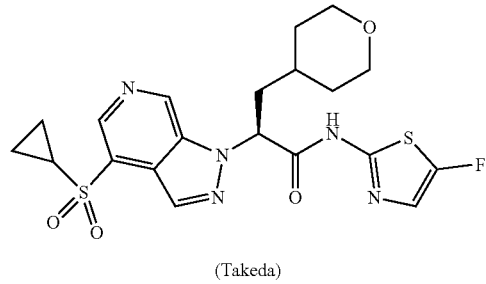
(Takeda)
2
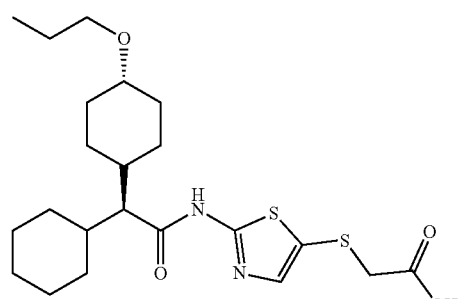
(TTP 399)
3
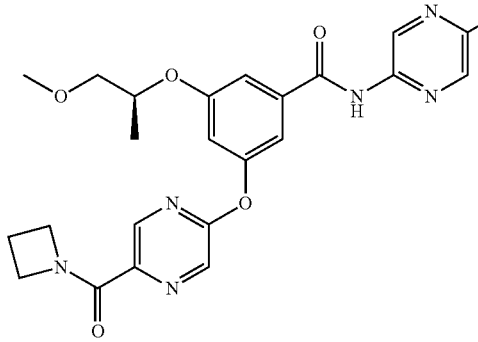
(AZD1656)
4
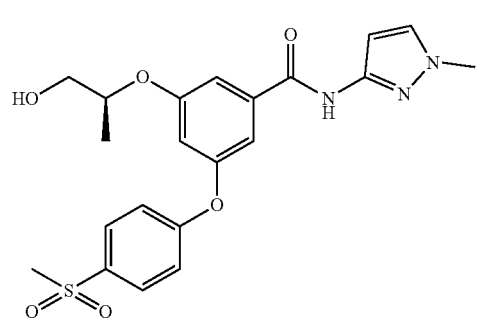
(AZD6370)
5
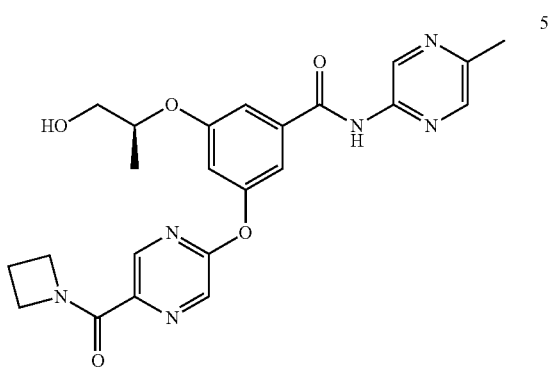
6
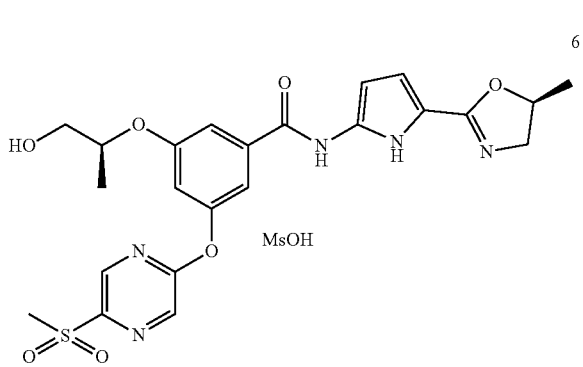

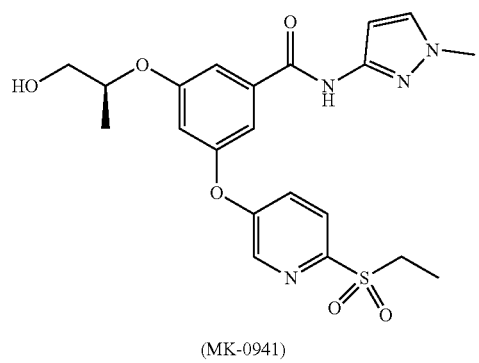
(MK-0941)
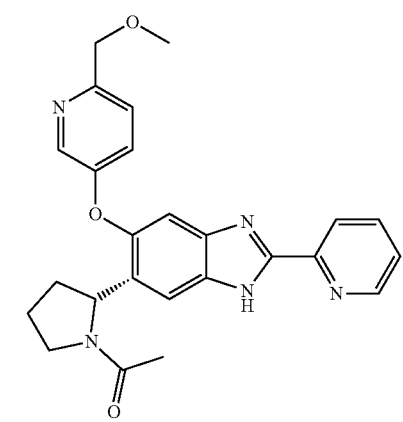
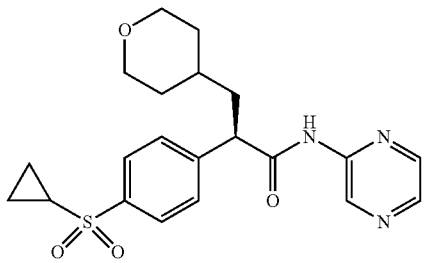
(LY2599506)
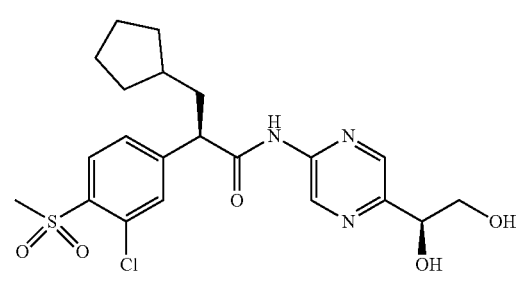
(LY2608204)
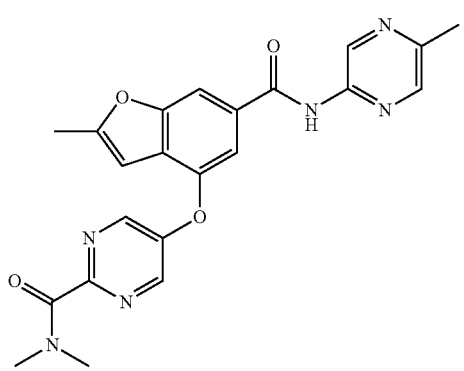
(PF-04937319)
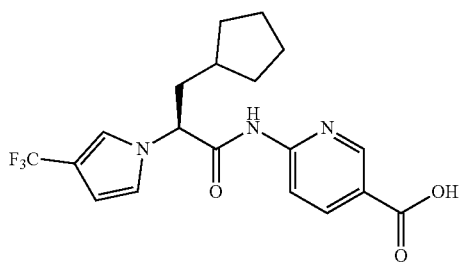
(PF-04991532)
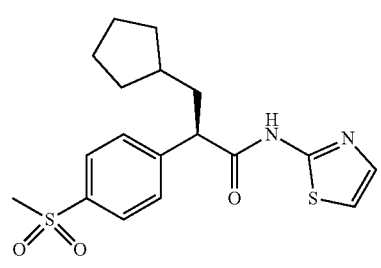
(R-1675)
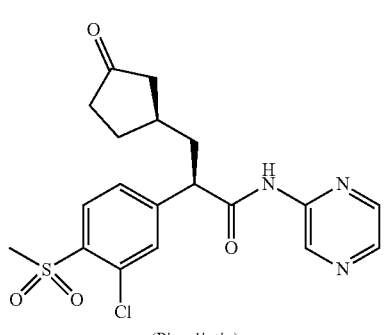
(Piragliatin)
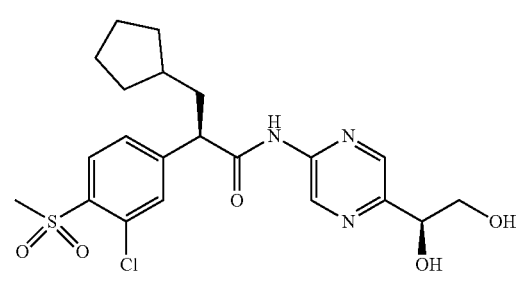
(RO4597014)

-continued

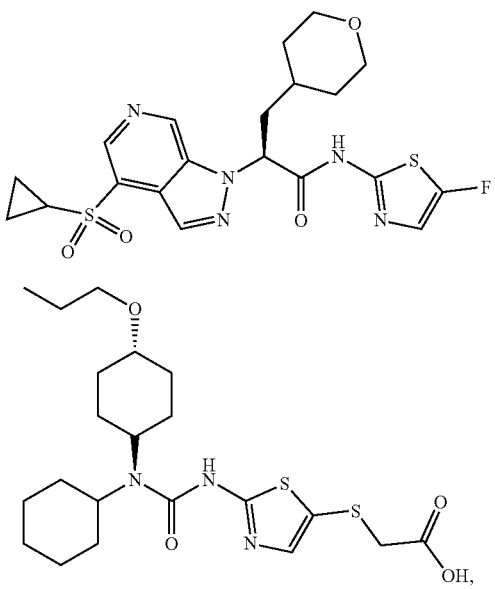

or isotope labeled analogues or pharmaceutically acceptable salts thereof.

In one embodiment, the disclosure relates to a solid dispersion, wherein the glucokinase activator is selected from the group consisting of TTP399, PF-04937319, RO4597014 and LY2608204, or isotope labeled analogues or pharmaceutically acceptable salts thereof.

In one embodiment, the disclosure relates to a solid dispersion, wherein the polymer carriers are controlled release carriers.

In one embodiment, the disclosure relates to a solid dispersion, wherein the polymer carriers are polyacrylic resin polymers.

In one embodiment, the disclosure relates to a solid dispersion, wherein the polymer carriers are selected from the group consisting of methacrylic acid copolymer and methacrylate copolymer.

In one embodiment, the disclosure relates to a solid dispersion, wherein the polymer carriers are selected from the group consisting of copolymer of butyl methacrylate, dimethylaminoethyl methacrylate and methyl methacrylate; copolymer of methacrylic acid and ethyl acrylate; copolymer of methacrylic acid and methyl methacrylate; copolymer of ethyl acrylate, methyl methacrylate and chlorotrimethylamino ethyl methacrylate; copolymer of ethyl acrylate and methyl methacrylate; copolymer of methacrylic acid, methyl acrylate and methyl methacrylate; copolymer of methacrylic acid and butyl acrylate.

In one embodiment, the disclosure relates to an oral formulation of the glucokinase activator, wherein the polymer carriers are selected from the group consisting of butyl methacrylate, copolymer of dimethylaminoethyl methacrylate and methyl methacrylate (1:2:1), copolymer of methacrylic acid and ethyl acrylate (1:1), copolymer of methacrylic acid and methyl methacrylate (1:2), copolymer of ethyl acrylate, methyl methacrylate and chlorotrimethylamino ethyl methacrylate (1:2:0.2), copolymer of ethyl acrylate, methyl methacrylate, and chlorotrimethylamino ethyl methacrylate (1:2:0.1), copolymer of ethyl acrylate and methyl methacrylate (2:1), copolymer of methacrylic acid and butyl acrylate (35:65), copolymer of methacrylic acid and methyl methacrylate (1:1), copolymer of methacrylic acid and methyl methacrylate (1:1), copolymer of methacrylic acid and methyl methacrylate (35:65).

In one embodiment, the disclosure relates to a solid dispersion, wherein the polymer carrier is selected from Eudragit.

In one embodiment, the disclosure relates to a solid dispersion, wherein the polymer carriers are selected from the group consisting of Eudragit E, Eudragit L, Eudragit S.

In one embodiment, the disclosure relates to a solid dispersion, wherein the polymer carriers are selected from the group consisting of Eudragit L100, Eudragit S 100, Eudragit E PO, Eudragit E 100 and Eudragit L 100-55.

In one embodiment, the disclosure relates to a solid dispersion, wherein the polymer carriers are Eudragit L100, i.e., methacrylic acid copolymer A TYPE, which is anion copolymer of methacrylic acid and methyl methacrylate (1:1).

In one embodiment, the disclosure relates to a solid dispersion, wherein the weight ratio of the glucokinase activator to polymer carriers is 1:10 to 10:1.

In one embodiment, the disclosure relates to a solid dispersion, wherein the weight ratio of the glucokinase activator to polymer carriers is 1:9 to 9:1, 1:4 to 4:1, 3:7 to 7:3, 2:3 to 3:2, 3:4 to 4:3, 4:5 to 5:4 or 5:6 to 6:5.

In one embodiment, the disclosure relates to a solid dispersion, wherein the weight ratio of the glucokinase activator to polymer carriers is 1:1.

In one embodiment, the disclosure relates to a solid dispersion, wherein the amount of the glucokinase activator accounts for 10 weight % to 90 weight % of the solid dispersion.

In one embodiment, the disclosure relates to a solid dispersion, wherein the amount of the glucokinase activator accounts for 30 weight % to 80 weight % of the solid dispersion.

In one embodiment, the disclosure relates to a solid dispersion, wherein the amount of the glucokinase activator accounts for 40 weight % to 80 weight % of the solid dispersion.

In one embodiment, the disclosure relates to a solid dispersion, wherein the amount of the glucokinase activator accounts for 50 weight % to 80 weight % of the solid dispersion.

In one embodiment, the disclosure relates to a solid dispersion, wherein the amount of the glucokinase activator accounts for 50 weight % of the solid dispersion.

In one embodiment, the disclosure relates to a solid dispersion, wherein the amount of polymer carriers accounts for 10 weight % to 90 weight % of the solid dispersion.

In one embodiment, the disclosure relates to a solid dispersion, wherein the solid dispersion is obtained by spray drying.

In one embodiment, the disclosure relates to a solid dispersion composition, which comprises the solid dispersion of the disclosure and excipients.

In one embodiment, the disclosure relates to a solid dispersion composition, wherein the excipients are selected from one or more consisting of diluent, sweeteners or flavoring agents, surfactants, fillers, binders, disintegrants, lubricants, glidant/antiadherents, release modifiers, stabilizers, coating agents, emulsifier and/or solubilizer, and perfumes.

In one embodiment, the disclosure relates to an oral formulation of the glucokinase activator, which comprises the solid dispersion or the solid dispersion composition.

In one embodiment, the disclosure relates to an oral formulation of the glucokinase activator, which is the oral, modified release formulation of the glucokinase activator.

In one embodiment, the disclosure relates to an oral formulation of the glucokinase activator, which is the oral, modified release, solid formulation of the glucokinase activator.

In one embodiment, the disclosure relates to an oral formulation of the glucokinase activator, wherein the oral, modified release, solid formulation of the glucokinase activator is selected from the group consisting of tablet, capsule, granule, powder, lozenge and pill.

In one embodiment, the disclosure relates to an oral formulation of the glucokinase activator, wherein the oral, modified release, solid formulation of the glucokinase activator is tablet.

In one embodiment, the disclosure relates to an oral formulation of the glucokinase activator, wherein the tablet comprises the solid dispersion of the disclosure, the fillers, the binders, the disintegrants and the lubricants.

In one embodiment, the disclosure relates to an oral formulation of the glucokinase activator, wherein in the tablet the content of solid dispersion of the glucokinase activator is 1 weight % to 90 weight %, the content of fillers is 1 weight % to 95 weight %, the content of binders is 0.5 weight % to 10 weight %, the content of disintegrants is 0.5 weight % to 7.5 weight %, and the content of lubricants is 0.25 weight % to 5 weight %.

In one embodiment, the disclosure relates to an oral formulation of the glucokinase activator, wherein in the tablet the fillers is silicified microcrystalline cellulose, microcrystalline cellulose or lactose, the binders is hydroxypropyl cellulose, hydroxypropylmethyl cellulose or polyvinyl pyrrolidone, the disintegrants is croscarmellose sodium or sodium carboxymethyl starch, and the lubricants is magnesium stearate or sodium stearyl fumarate.

In one embodiment, the disclosure relates to an oral formulation of the glucokinase activator, wherein in the tablet the filler is silicified microcrystalline cellulose, the binder is hydroxypropyl cellulose, the disintegrant is croscarmellose sodium, and the lubricant is magnesium stearate.

In one embodiment, the disclosure relates to an oral formulation of the glucokinase activator, wherein the tablet is coated tablet.

In one embodiment, the disclosure relates to an oral formulation of the glucokinase activator, wherein the coated tablet comprise coating agents which are selected from the group consisting of sodium carboxymethylcellulose, cellulose acetate, cellulose acetate phthalate, ethylcellulose, gelatin, pharmaceutical glaze, hydroxypropyl cellulose, hydroxypropylmethyl cellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcrystalline wax, zein and Opadry.

In one embodiment, the disclosure relates to an oral formulation of the glucokinase activator, wherein the coating agent in the coated tablet is Opadry.

In one embodiment, the disclosure relates to an oral formulation of the glucokinase activator, wherein in the coated tablet the content of the solid dispersion of the glucokinase activator is 1 weight % to 90 weight %, the content of fillers is 1 weight % to 95 weight %, the content of binders is 0.5 weight % to 10 weight %, the content of disintegrants is 0.5 weight % to 7.5 weight %, the content of lubricants is 0.25 weight % to 5 weight %, and the content of coating agents is 1 weight % to 10 weight %.

In one embodiment, the disclosure relates to an oral formulation of the glucokinase activator, wherein the capsule is gelatin capsule, HPMC capsule of plant origin, enteric capsule or soft capsule.

In one embodiment, the disclosure relates to an oral formulation of the glucokinase activator, wherein the capsule comprises the solid dispersion of the disclosure, fillers and/or binder, and/or disintegrant and/or lubricant.

In one embodiment, the disclosure relates to an oral formulation of the glucokinase activator, wherein in the capsule formulation the content of the solid dispersion is 1 weight % to 90 weight %, the content of fillers is 5 weight % to 95 weight %, the content of binders is 0 weight % to 10 weight %, the content of disintegrants is 0.5 weight % to 7.5 weight %, and the content of lubricants is 0 weight % to 5 weight %.

In one embodiment, the disclosure relates to an oral formulation of the glucokinase activator, wherein in the capsule formulation the content of the solid dispersion is 1 weight % to 90 weight %, the content of fillers is 5 weight % to 95 weight %, and the content of binders is 0.5 weight % to 10 weight %.

In one embodiment, the disclosure relates to an oral formulation of the glucokinase activator, wherein in the capsule formulation the content of the solid dispersion is 1 weight % to 90 weight %, the content of fillers is 5 weight % to 95 weight %, and the content of disintegrants is 0.5 weight % to 7.5 weight %.

In one embodiment, the disclosure relates to an oral formulation of the glucokinase activator, wherein in the capsule the filler is silicified microcrystalline cellulose, the binder is hydroxypropyl cellulose, the disintegrant is croscarmellose sodium and the lubricant is magnesium stearate.

In one embodiment, the disclosure relates to an oral formulation of the glucokinase activator, which has a dissolution rate of <45% at pH 1.2~4.5 at 30 min, and a dissolution rate of >85% at pH 6.0~7.0 at 30 min.

In one embodiment, the disclosure relates to an oral formulation of the glucokinase activator wherein the tablet has a dissolution rate of <40% at pH 1.2~4.5 at 30 min, and a dissolution rate of >85% at pH 6.0~7.0 at 30 min.

In one embodiment, the disclosure relates to an oral formulation of the glucokinase activator which is tablet having a dissolution rate of <30% at pH 1.2 at 30 min, a dissolution rate of <40% at pH 4.5 at 30 min, and a dissolution rate of >85% at pH 6.8 at 30 min.

In one embodiment, the disclosure relates to an oral formulation of the glucokinase activator, wherein the tablet is coated tablet, which has a dissolution rate of is <30% at pH 1.2 at 30 min, a dissolution rate of <40% at pH 4.5 at 30 min, and a dissolution rate of >85% at pH 6.8 at 30 min.

In one embodiment, the disclosure relates to an oral formulation of the glucokinase activator which is capsule having a dissolution rate of <45% at pH 1.2 at 30 min, a dissolution rate of <45% at pH 4.5 at 30 min, and a dissolution rate of >85% at pH 6.8 at 30 min.

In one embodiment, the disclosure relates to an oral formulation of the glucokinase activator, wherein in a unit formulation the amount of the glucokinase activator is about 1 mg to about 200 mg, and in a further embodiment, is about 2 mg to about 150 mg, in a further embodiment, is about 2.5 mg to about 150 mg, in a further embodiment, is about 5 mg to about 150 mg, and in a further embodiment, is about 5 mg to about 100 mg.

In one embodiment, the disclosure relates to an oral formulation of the glucokinase activator, wherein in a unit tablet the amount of the glucokinase activator is about 1 mg to about 200 mg, about 2 mg to about 150 mg, about 2.5 mg to about 150 mg, about 5 mg to about 150 mg or about 5 mg to about 100 mg.

In one embodiment, the disclosure relates to an oral formulation of the glucokinase activator, wherein in a unit coated tablet the amount of the glucokinase activator is about 1 mg to about 200 mg, about 2 mg to about 150 mg, about 2.5 mg to about 150 mg, about 5 mg to about 150 mg or about 5 mg to about 100 mg.

In one embodiment, the disclosure relates to the use of the solid dispersion, the solid dispersion composition or the oral formulation of the glucokinase activator in the preparation of a medicament for treating and/or preventing the selected diseases and disorders, particularly one or more diseases and disorders selected from the group consisting of type I diabetes, type II diabetes, impaired glucose tolerance, impaired fasting glucose and hyperglycemia.

In one embodiment, the disclosure relates to a method of treating and/or preventing the selected diseases and disorders, particularly one or more diseases or disorders selected from the group consisting of type I diabetes, type II diabetes, impaired glucose tolerance, impaired fasting glucose and hyperglycemia by the solid dispersion, the solid dispersion composition or the oral formulation of the glucokinase activator, comprising administering to a patient a therapeutically effective amount of the solid dispersion, the solid dispersion composition or the oral formulation of the glucokinase activator of the disclosure.

In one embodiment, the disclosure relates to a method of preparing the solid dispersion of the disclosure, including melting method, solvent method, solvent-melting method, spray drying method, freeze drying method, and grinding method.

In one embodiment, the disclosure relates to a method of preparing the solid dispersion of the disclosure, which comprises the steps of:
(1) preparing the solution of spray drying, comprising dissolving a polymer carrier(s) and glucokinase activator(s) in a solvent;
(2) spray drying;
wherein, the solvent is anhydrous ethanol, methanol, isopropanol, ethyl acetate, acetone, acetonitrile, isobutanol, n-hexane, benzene and toluene or a mixture thereof or a mixture of said solvent with water.

Particularly, in one embodiment of the disclosure, in the method of preparing the solid dispersion, in the spray drying step the temperature of inlet air is 90-150° C., the flow of inlet air is in the range of 0.3-0.5 m³/min, the flow rate of atomized gas is 10-30 L/min, and the speed of solution spray is 5-200 mL/min.

In one embodiment, the disclosure relates to an oral formulation of the glucokinase activator, which comprises the solid dispersion of the glucokinase activator or the solid dispersion composition and excipients.

In one embodiment, the disclosure relates to an oral formulation of the glucokinase activator, wherein the solid dispersion of the glucokinase activator comprise the glucokinase activator, or isotope labeled analogues thereof or pharmaceutically acceptable salts thereof and polymer carriers.

In one embodiment, the disclosure relates to an oral formulation of the glucokinase activator, wherein the glucokinase activator is a compound of formula (Ia)

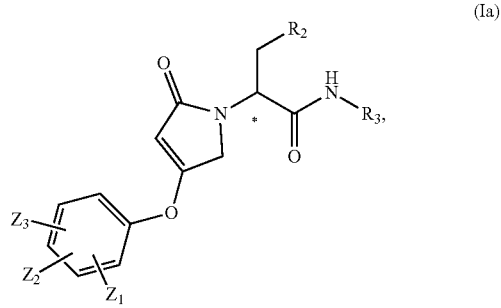

(Ia)

wherein:

$Z_1$, $Z_2$, $Z_3$ independently of each other, are hydrogen, lower alkyl, lower alkenyl, hydroxy, —$NH_2$, halogen, lower alkoxy, —$CF_3$, —$OCF_3$, —$S(CH_3)$, —$S(O_2)CH_3$, —$CH_2$-aryl, heteroaryl, cyano, lower alkanoyl, —O-aryl, —O—$CH_2$-aryl, —$N(CH_3)_2$, cycloalkyl, heterocyclyl, —C(O)-heterocyclyl, or lower alkyl mono- or di-substituted with hydroxy;

$R_2$ is selected from the group consisting of lower alkyl, lower alkyl mono- or di-substituted with hydroxy, lower haloalkyl, lower alkoxyalkyl, lower alkylthioalkyl, lower alkoxy, cycloalkyl, said cycloalkyl being unsubstituted or mono- or di-substituted independently with halogen or lower alkyl, heterocyclyl and aryl, said aryl being unsubstituted or mono- or di-substituted independently with halogen; and $R_3$ is -lower alkyl-carbamoyl or an unsubstituted or substituted heteroaryl connected through a ring carbon atom to the amine group as shown, wherein one of the heteroatoms is nitrogen and it is adjacent to the connecting ring carbon atom, said substituted heteroaryl is substituted at a position other than positions adjacent to said connecting carbon atom independently with a group selected from the group consisting of:

lower alkyl, halogen, lower alkoxycarbonyl, cyano, carboxyl, cycloalkyl, aryl, 2-oxo-oxazolidin-5-ylmethyl, —N(lower alkyl)$_2$, 2,2-dimethyl-[1,3]dioxolan-4-yl, —$CH_2$-dimethyl-[1,3]dioxolane, t-butyl-dimethyl-silanyloxy-ethyl, unsubstituted —$CH_2$-aryl, —$CH_2$-aryl substituted with cyano or alkoxy, heterocyclyl, —$CH_2$-heterocyclyl, -6-($CH_2$)-2,2-dimethyl-[1,3]dioxan-4-yl-acetic acid tert-butyl ester, and lower alkyl mono-, di- or tri-substituted independently with hydroxy, halogen, alkoxy, —N(lower alkyl)$_2$, —$NH_2$, lower alkanoyl, lower alkoxycarbonyl, lower alkenyloxycarbonyl, carboxyl, aminocarbonyl or lower alkoxycarbonylamino, or isotope labeled analogues or pharmaceutically acceptable salts thereof.

In one embodiment, the disclosure relates to an oral formulation of the glucokinase activator, wherein the glucokinase activator is selected from the group consisting of the following compounds or isotope labeled analogues or pharmaceutically acceptable salts thereof:

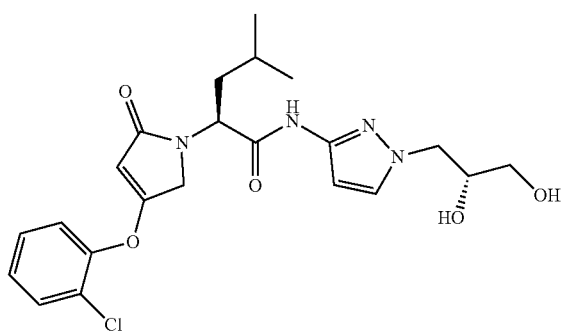
HMS5552

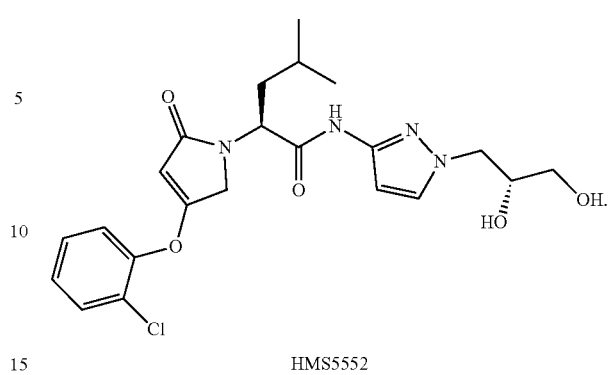
HMS5552

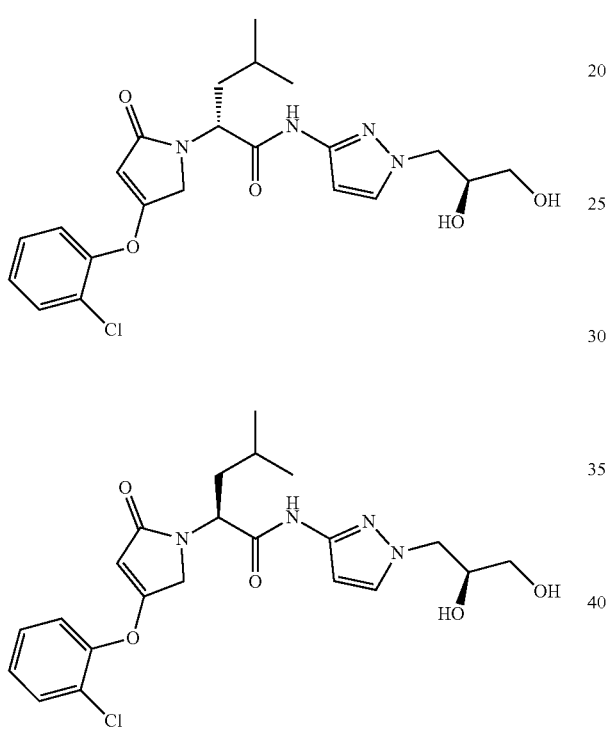

In one embodiment, the disclosure relates to an oral formulation of the glucokinase activator, wherein the glucokinase activator is the compound HMS5552 or isotope labeled analogues thereof or pharmaceutically acceptable salts thereof.

In one embodiment, the disclosure relates to an oral formulation of the glucokinase activator, wherein the glucokinase activator is selected from the group consisting of:

1

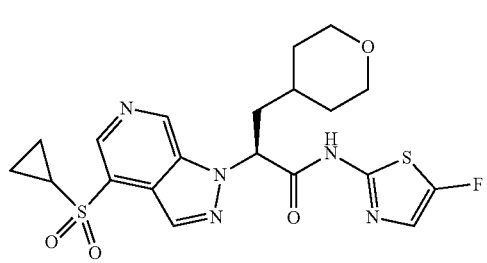
(Takeda)

2

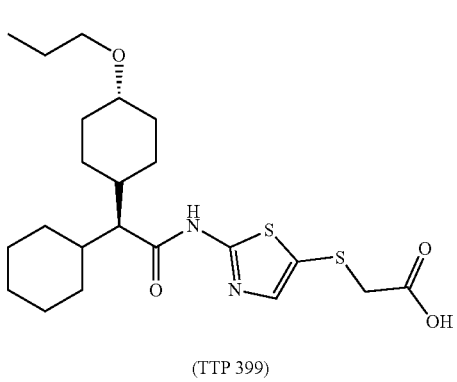
(TTP 399)

3

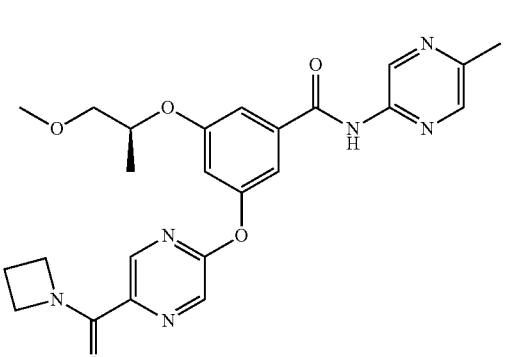
(AZD1656)

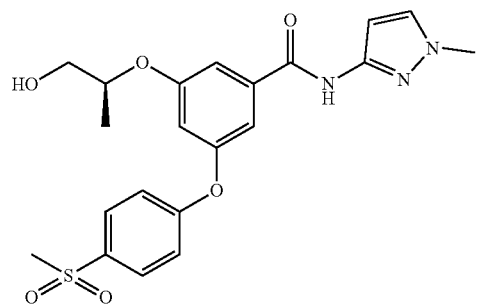
(AZD6370)
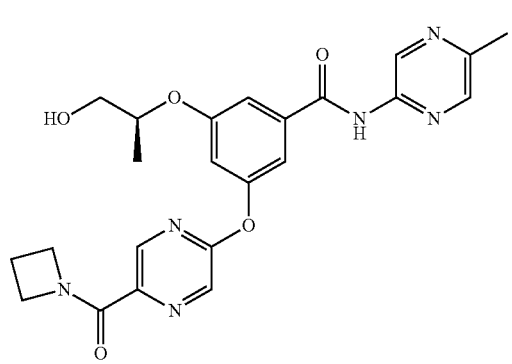
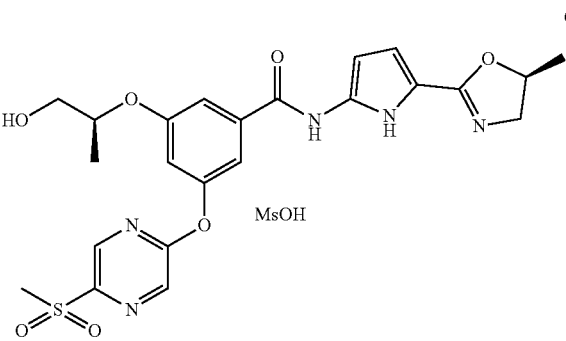
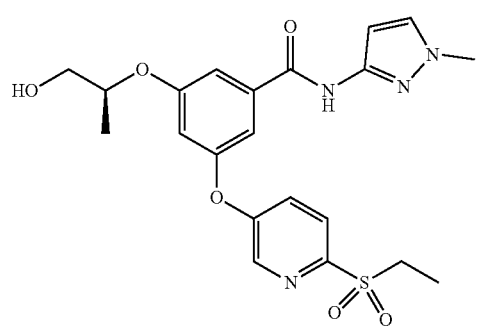
(MK-0941)
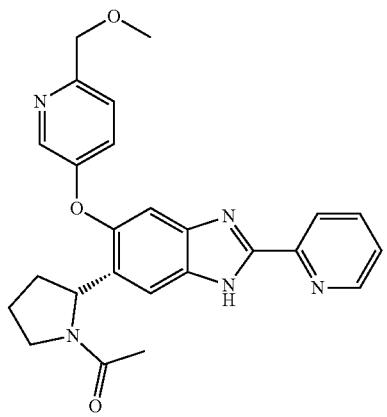
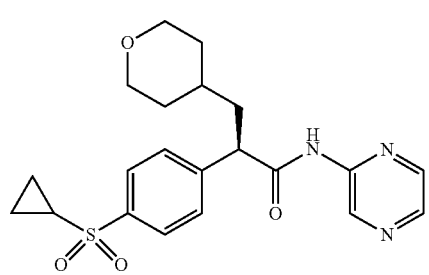
(LY2599506)
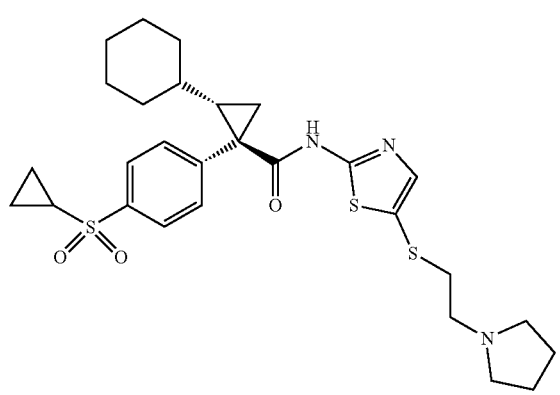
(LY2608204)
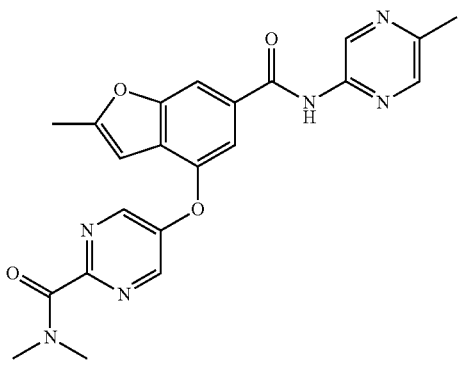
(PF-04937319)

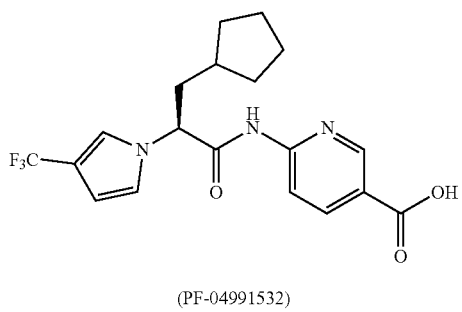

(PF-04991532)

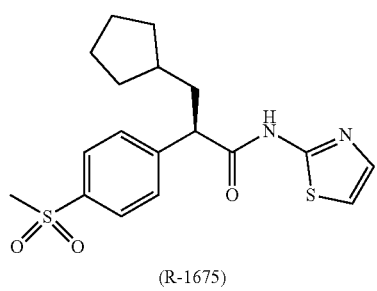

(R-1675)

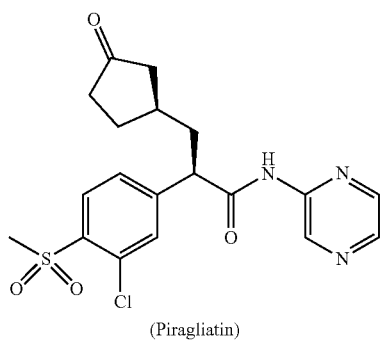

(Piragliatin)

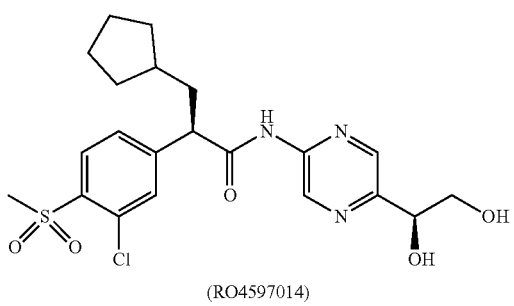

(RO4597014)

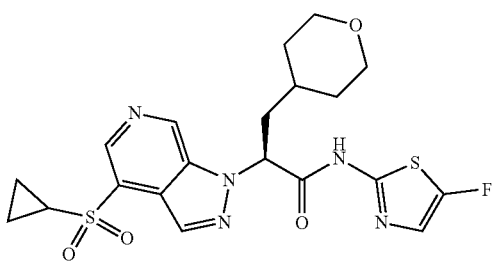

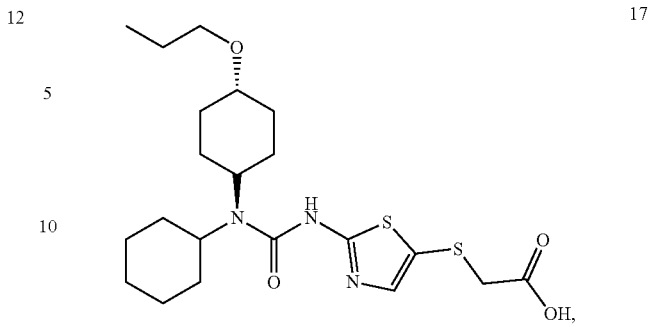

or isotope labeled analogues thereof or pharmaceutically acceptable salts thereof.

In one embodiment, the disclosure relates to an oral formulation of the glucokinase activator, wherein the glucokinase activator is selected from the group consisting of TTP399, PF-04937319, RO4597014 and LY2608204, isotope labeled analogues or pharmaceutically acceptable salts thereof.

In one embodiment, the disclosure relates to an oral formulation of the glucokinase activator, wherein the polymer carriers are controlled release carriers.

In one embodiment, the disclosure relates to an oral formulation of the glucokinase activator, wherein the polymer carriers are polyacrylic resin polymers.

In one embodiment, the disclosure relates to an oral formulation of the glucokinase activator, wherein the polymer carriers are selected from the group consisting of methacrylic acid copolymer and methacrylate copolymer.

In one embodiment, the disclosure relates to an oral formulation of the glucokinase activator, wherein the polymer carriers are selected from the group consisting of copolymer of butyl methacrylate, dimethylaminoethyl methacrylate and methyl methacrylate; copolymer of methacrylic acid and ethyl acrylate; copolymer of methacrylic acid and methyl methacrylate; copolymer of ethyl acrylate, methyl methacrylate and chlorotrimethylamino ethyl methacrylate; copolymer of ethyl acrylate and methyl methacrylate; copolymer of methacrylic acid, methyl acrylate and methyl methacrylate; copolymer of methacrylic acid and butyl acrylate.

In one embodiment, the disclosure relates to an oral formulation of the glucokinase activator, wherein the polymer carriers are selected from the group consisting of copolymer of butyl methacrylate, dimethylaminoethyl methacrylate and methyl methacrylate (1:2:1), copolymer of methacrylic acid and ethyl acrylate (1:1), copolymer of methacrylic acid and methyl methacrylate (1:2), copolymer of ethyl acrylate, methyl methacrylate and chlorotrimethylamino ethyl methacrylate (1:2:0.2), copolymer of ethyl acrylate, methyl methacrylate and chlorotrimethylamino ethyl methacrylate (1:2:0.1), copolymer of ethyl acrylate and methyl methacrylate (2:1), copolymer of methacrylic acid and butyl acrylate (35:65), copolymer of methacrylic acid and methyl methacrylate (1:1), copolymer of methacrylic acid and methyl methacrylate (1:1), copolymer of methacrylic acid and methyl methacrylate (35:65).

In one embodiment, the disclosure relates to an oral formulation of the glucokinase activator, wherein the polymer carrier is selected from Eudragit.

In one embodiment, the disclosure relates to an oral formulation of the glucokinase activator, wherein the polymer carriers are selected from the group consisting of Eudragit E, Eudragit L, Eudragit S.

In one embodiment, the disclosure relates to an oral formulation of the glucokinase activator, wherein the polymer carriers are selected from the group consisting of Eudragit L100, Eudragit S100, Eudragit E PO, Eudragit E 100 or Eudragit L100-55.

In one embodiment, the disclosure relates to an oral formulation of the glucokinase activator, wherein the polymer carriers are Eudragit L100, which is methacrylic acid copolymer A TYPE, and anion copolymer of methacrylic acid and methyl methacrylate (1:1). In one embodiment, the disclosure relates to an oral formulation of the glucokinase activator, wherein the amount of the glucokinase activator accounts for 10 weight % to 90 weight % of the solid dispersion.

In one embodiment, the disclosure relates to an oral formulation of the glucokinase activator, wherein the amount of the glucokinase activator accounts for 30 weight % to 80 weight % of the solid dispersion.

In one embodiment, the disclosure relates to an oral formulation of the glucokinase activator, wherein the amount of the glucokinase activator accounts for 40 weight % to 80 weight % of the solid dispersion.

In one embodiment, the disclosure relates to an oral formulation of the glucokinase activator, wherein the amount of the glucokinase activator accounts for 50 weight % to 80 weight % of the solid dispersion.

In one embodiment, the disclosure relates to an oral formulation of the glucokinase activator, wherein the amount of the glucokinase activator accounts for 50 weight % of the solid dispersion.

In one embodiment, the disclosure relates to an oral formulation of the glucokinase activator, wherein the amount of polymer carriers comprises 10 weight % to 90 weight % of the solid dispersion.

In one embodiment, the disclosure relates to an oral formulation of the glucokinase activator, wherein the solid dispersion is obtained by spray drying.

In one embodiment, the disclosure relates to an oral formulation of the glucokinase activator, wherein the excipients are selected from one or more of: diluent; sweetener or flavoring agent; surfactant; filler; binder; disintegrant; lubricant; glidant/antiadherent; release modifier; stabilizer; coating agents; emulsifier and/or solubilizer and perfumes.

In one embodiment, the disclosure relates to an oral formulation of the glucokinase activator, which is an oral, modified release formulation of the glucokinase activator.

In one embodiment, the disclosure relates to an oral formulation of the glucokinase activator, which is an oral, modified release, solid formulation of the glucokinase activator.

In one embodiment, the disclosure relates to an oral formulation of the glucokinase activator, wherein the oral, modified release, solid formulation of the glucokinase activator is selected from the group consisting of tablet, capsule, granule, powder, lozenge and pill.

In one embodiment, the disclosure relates to an oral formulation of the glucokinase activator, which comprises the solid dispersion of the disclosure, and/or fillers, and/or binders, and/or disintegrants, and/or lubricants.

In one embodiment, the disclosure relates to an oral formulation of the glucokinase activator, wherein the oral, modified release solid formulation of the glucokinase activator is tablet.

In one embodiment, the disclosure relates to an oral formulation of the glucokinase activator, wherein the tablet comprises the solid dispersion of the disclosure, fillers, binders, disintegrants and lubricants.

In one embodiment, the disclosure relates to an oral formulation of the glucokinase activator, wherein in the tablet, the content of the solid dispersion of the glucokinase activator is 1 weight % to 90 weight %, the content of fillers is 1 weight % to 95 weight %, the content of binders is 0.5 weight % to 10 weight %, the content of disintegrants is 0.5 weight % to 7.5 weight %, and the content of lubricants is 0.25 weight % to 5 weight %.

In one embodiment, the disclosure relates to an oral formulation of the glucokinase activator, wherein in the tablet, the filler is silicified microcrystalline cellulose, microcrystalline cellulose or lactose, the binder is hydroxypropyl cellulose, hydroxypropylmethyl cellulose or polyvinyl pyrrolidone, the disintegrant is croscarmellose sodium or sodium carboxymethyl starch, and the lubricant is magnesium stearate or sodium stearyl fumarate.

In one embodiment, the disclosure relates to an oral formulation of the glucokinase activator, wherein in the tablet the filler is silicified microcrystalline cellulose, the binder is hydroxypropyl cellulose, the disintegrant is croscarmellose sodium, and the lubricant is magnesium stearate.

In one embodiment, the disclosure relates to an oral formulation of the glucokinase activator, wherein the tablet is coated tablet.

In one embodiment, the disclosure relates to an oral formulation of the glucokinase activator, wherein the coated tablet comprises coating agents selected from the group consisting of sodium carboxymethylcellulose, cellulose acetate, cellulose acetate phthalate, ethylcellulose, gelatin, pharmaceutical glaze, hydroxypropyl cellulose, hydroxypropylmethyl cellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcystalline wax, zein and Opadry.

In one embodiment, the disclosure relates to an oral formulation of the glucokinase activator, wherein the coating agent in the coated tablet is Opadry.

In one embodiment, the disclosure relates to an oral formulation of the glucokinase activator, wherein in the coated tablet, the content of the solid dispersion of the glucokinase activator is 1 weight % to 90 weight %, the content of filler is 1 weight % to 95 weight %, the content of binder is 0.5 weight % to 10 weight %, the content of disintegrant is 0.5 weight % to 7.5 weight %, the content of lubricant is 0.25 weight % to 5 weight %, and the content of coating agents is 1 weight % to 10 weight %.

In one embodiment, the disclosure relates to an oral formulation of the glucokinase activator, wherein the capsule is gelatin capsule, HPMC capsule of plant origin, enteric capsule or soft capsule.

In one embodiment, the disclosure relates to an oral formulation of the glucokinase activator, wherein the capsule comprises the solid dispersion of the disclosure, fillers and/or binders and/or disintegrants and/or lubricants.

In one embodiment, the disclosure relates to an oral formulation of the glucokinase activator, wherein in the capsule, the content of the solid dispersion is 1 weight % to 90 weight %, the content of fillers is 5 weight % to 95 weight %, and/or the content of the binders is 0 weight % to 10 weight %, and/or the content of disintegrants is 0.5 weight % to 7.5 weight %, and/or the content of lubricants is 0 weight % to 5 weight %.

In one embodiment, the disclosure relates to an oral formulation of the glucokinase activator, wherein in the capsule the filler is silicified microcrystalline cellulose, the binder is hydroxypropyl cellulose, the disintegrant is croscarmellose sodium and the lubricant is magnesium stearate.

In one embodiment, the disclosure relates to an oral formulation of the glucokinase activator, which has a dissolution rate of <45% at pH 1.2~4.5 at 30 min, and a dissolution rate of >85% at pH 6.0~7.0 at 30 min.

In one embodiment, the disclosure relates to an oral formulation of the glucokinase activator, which is a tablet having a dissolution rate of <40% at pH 1.2~4.5 at 30 min, and a dissolution rate of >85% at pH 6.0~7.0 at 30 min.

In one embodiment, the disclosure relates to an oral formulation of the glucokinase activator, which is a tablet having a dissolution rate of <30% at pH 1.2 at 30 min, a dissolution rate of <40% at pH 4.5 at 30 min, and a dissolution rate of >85% at pH 6.8 at 30 min.

In one embodiment, the disclosure relates to an oral formulation of the glucokinase activator, wherein the tablet is coated tablet having a dissolution rate of <30% at pH 1.2 at 30 min, a dissolution rate of <40% at pH 4.5 at 30 min, and a dissolution rate of >85% at pH 6.8 at 30 min.

In one embodiment, the disclosure relates to an oral formulation of the glucokinase activator, which is a capsule having a dissolution rate of <45% at pH 1.2 at 30 min, a dissolution rate of <45% at pH 4.5 at 30 min, and a dissolution rate of >85% at pH 6.8 at 30 min.

In one embodiment, the disclosure relates to an oral formulation of the glucokinase activator, wherein in a unit formulation, the amount of the glucokinase activator is about 1 mg to about 200 mg, in one embodiment is about 2 mg to about 150 mg, in one embodiment is about 2.5 mg to about 150 mg, in one embodiment is about 5 mg to about 150 mg, and in one embodiment is about 5 mg to about 100 mg.

In one embodiment, the disclosure relates to an oral formulation of the glucokinase activator, wherein in a unit tablet, the amount of the glucokinase activator is about 1 mg to about 200 mg, about 2 mg to about 150 mg, about 2.5 mg to about 150 mg, about 5 mg to about 150 mg or about 5 mg to about 100 mg.

In one embodiment, the disclosure relates to an oral formulation of the glucokinase activator, wherein in a unit coated tablet, the amount of the glucokinase activator is about 1 mg to about 200 mg, about 2 mg to about 150 mg, about 2.5 mg to about 150 mg, about 5 mg to about 150 mg or about 5 mg to about 100 mg.

In one embodiment, the disclosure relates to the use of the the oral formulation of the glucokinase activator in the preparation of a medicament for treating and/or preventing the selected diseases and disorders, particularly one or more diseases and disorders selected from the group consisting of type I diabetes, type II diabetes, impaired glucose tolerance, impaired fasting glucose and hyperglycemia.

In one embodiment, the disclosure relates to a method of treating and/or preventing the selected diseases and disorders, particularly one or more diseases and disorders selected from the group consisting of type I diabetes, type II diabetes, impaired glucose tolerance, impaired fasting glucose and hyperglycemia by the oral formulation of the glucokinase activator, comprising administering to the patient a therapeutically effective amount of the oral formulation of the glucokinase activator of the disclosure.

In one embodiment, the disclosure relates to a method of preparing the solid dispersion, which comprises the steps of:
(1) preparing the solution of spray drying, including dissolving polymer carriers and the glucokinase activator in a solvent;
(2) spray drying;
Wherein the solvent is anhydrous ethanol, methanol, isopropanol, ethyl acetate, acetone, acetonitrile, isobutanol, n-hexane, benzene and toluene or a mixture thereof or a mixture of the solvent with water.

Particularly, in the spray drying step the inlet air temperature is 90-150° C., the flow rate of the inlet air is in the range of 0.3-0.5 m$^3$/min, the flow rate of atomized gas is 10-30 L/min, and the speed of solution spray is 5-200 mL/min.

In one embodiment, the disclosure relates to the preparation method of the oral tablet of the glucokinase activator, which comprises the steps of:
(1) weighing and sieving: weighing a prescriptive amount of each component, wherein the lubricant is sieved before use;
(2) granulating: a. adding the intragranular fillers, the solid dispersion and binders into a wet granulator, premixing according to the preset parameters, and adding the weighed pure water for the wet granulation, and then after discharging, wet granulating the granules by a mill, and drying (box-type drying or fluidized bed drying), and then dry granulating the granules by a mill; or b. adding the intragranular fillers and the solid dispersion into a wet granulator, premixing according to the preset parameters, adding the prepared solution of binder for wet granulation, and then after discharging, wet granulating the granules by a mill, and drying (box-type drying or fluidized bed drying), and then dry granulating the granules by a mill;
(3) mixing: weighing the granules actually obtained, adding extragranular fillers, disintegrants and lubricants in proportion, and mixing;
(4) pressing: loading the mixed granules into a rotary tablet press and starting to compress.

In one embodiment, the disclosure relates to the method of preparing the coated tablet of the glucokinase activator, which comprises the steps of:
(1) preparing the tablets of the glucokinase activator;
(2) preparing the coating solution: preparing the coating suspension under uniform agitation;
(3) coating: weighing tablets of the glucokinase activator, adding into a coating pan, spraying the coating solution to coat the tablets, and then discharging the cotated tablets.

The present disclosure also relates to isotopically-labelled glucokinase activators which are identical to those recited herein, except the fact that one or more atoms are replaced by the atom having an atomic mass or mass number different from that usually found in nature.

Examples of isotopes that can be incorporated into compounds of the disclosure include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labelled compounds (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., H) may afford therapeutic advantages resulting from greater metabolic stability (e.g., increased in vivo half-life or reduced dosage requirements) and hence may be preferred in some circumstances. Isotopically labelled compounds can generally be prepared by procedures analogous to those disclosed in the Schemes and/or in the Examples hereinbelow, by substituting the non-isotopically labelled reagent with an appropriately isotopically labelled reagent.

In one embodiment of the disclosure, the oral modified release formulation is oral solid formulation and oral liquid formulation.

In one embodiment of the disclosure, the oral, solid formulation is selected from the group consisting of tablet, capsule, granule, powder, lozenge and pill.

In a further embodiment, the tablet is coated tablet.

In another aspect, the disclosure relates to a solid dispersion composition of the glucokinase activator, which comprises the solid dispersion of the glucokinase activator and excipients, and the excipients are selected from the group consisting of: diluent, for example diluent for tablet and/or capsule; sweetener or flavoring agent; antioxidant; surfactant; filler; binder; disintegrant, for example disintegrant for tablet; lubricant, for example lubricant for tablet and/or capsule; glidant/anti-adherent; release modifier; stabilizer; coating agents; colorant; chelating agent; emulsifier and/or solubilizer; flavoring agent and perfume; polymer carriers.

In the disclosure, the solid dispersion composition of the glucokinase activator disclosed herein can be used directly, or it can be made into different dosage forms according to the needs of treatment or prevention.

The solid dispersion composition of the glucokinase activator disclosed herein can be prepared into various dosage forms such as tablets, capsules, granules, powders, lozenge and pill, and can be produced by a known method. For example, the formulation may be prepared by formulating steps such as a mixing step, a granulation process, capsule filling or pressing and coating.

One embodiment of the present disclosure is a method of preparing the solid dispersion of the glucokinase activator of the present disclosure, and the method is selected from the group consisting of spray drying method, fluidized bed drying method, solvent method, melt extrusion method, and the like.

One embodiment of the present disclosure is the solid dispersion of the glucokinase activator prepared by the spray drying method, and the steps of the method include:

(1) preparing the solution of spray drying, comprising dissolving polymer carriers and the glucokinase activator in a solvent;

(2) spray drying, controlling the temperature and amount of inlet air, the flow rate and pressure of the atomizing gas stream as well as the spray rate of the solution, etc.

In the embodiments of the present disclosure, solvents for the solid dispersion formulation of the glucokinase activator include, but are not limited to, alkanols, esters, nitriles, cycloalkanes, aromatic hydrocarbons, ketones and the like. Specifically, the solvents are selected from the group consisting of anhydrous ethanol, methanol, isopropanol, ethyl acetate, acetone, acetonitrile, isobutanol, n-hexane, benzene and toluene. It may be a single solvent or a mixed solvent, or a mixture of organic solvent(s) with water.

In a further embodiment of the disclosure, it relates to a method of treating and/or preventing the selected diseases and disorders, particularly one or more diseases and disorders selected from the group consisting of type I diabetes, type II diabetes, impaired glucose tolerance, impaired fasting glucose and hyperglycemia by the solid dispersion or formulation of the glucokinase activator of the disclosure, comprising administering to a patient a therapeutically effective amount of the oral formulation of the glucokinase activator of the disclosure.

In a further embodiment of the disclosure, it relates to use of the solid dispersion of the glucokinase activator or the formulation comprising the composition in the preparation of a medicament for treating and/or preventing the selected diseases and disorders, particularly one or more diseases and disorders selected from the group consisting of type I diabetes, type II diabetes, impaired glucose tolerance, impaired fasting glucose and hyperglycemia.

The amount of the glucokinase activator used in the solid dispersion of the glucokinase activator disclosed herein may vary in the range from about 1 weight % to about 99 weight %, based on the total weight of the solid dispersion. In one embodiment, the range of content of the glucokinase activator is about 1 weight %, about 2 weight %, about 3 weight %, about 4 weight %, about 5 weight %, about 6 weight %, about 7 weight %, about 8 weight %, about 9 weight %, about 10 weight %, about 11 weight %, about 12 weight %, about 13 weight %, about 14 weight %, about 15 weight %, about 16 weight %, about 17 weight %, about 18 weight %, about 19 weight %, about 20 weight %, about 21 weight %, about 22 weight %, about 23 weight %, about 24 weight %, about 25 weight %, about 26 weight %, about 27 weight %, about 28 weight %, about 29 weight %, about 30 weight %, about 31 weight %, about 32 weight %, about 33 weight %, about 34 weight %, about 35 weight %, about 36 weight %, about 37 weight %, about 38 weight %, about 39 weight %, about 40 weight %, about 41 weight %, about 42 weight %, about 43 weight %, about 44 weight %, about 45 weight %, about 46 weight %, about 47 weight %, about 48 weight %, about 49 weight %, about 50 weight %, about 51 weight %, about 52 weight %, about 53 weight %, about 54 weight %, about 55 weight %, about 56 weight %, about 57 weight %, about 58 weight %, about 59 weight %, about 60 weight %, about 61 weight %, about 62 weight %, about 63 weight %, about 64 weight %, about 65 weight %, about 66 weight %, about 67 weight %, about 68 weight %, about 69 weight %, about 70 weight %, about 71 weight %, about 72 weight %, about 73 weight %, about 74 weight %, about 75 weight %, about 76 weight %, about 77 weight %, about 78 weight %, about 79 weight %, about 80 weight %, about 81 weight %, about 82 weight %, about 83 weight %, about 84 weight %, about 85 weight %, about 86 weight %, about 87 weight %, about 88 weight %, about 89 weight %, about 90 weight %, about 91 weight %, about 92 weight %, about 93 weight %, about 94 weight %, about 95 weight %, about 96 weight %, about 97 weight %, about 98 weight % or about 99 weight %, or any subrange therebetween. In one embodiment, the amount range of the glucokinase activator is about 1 weight % to about 20 weight %. In a further embodiment, the amount range of the glucokinase activator is about 2 weight % to about 40 weight %. In a further embodiment, the amount range of the glucokinase activator is about 30 weight % to about 60 weight %. In a further embodiment, the amount range of the glucokinase activator is about 60 weight % to about 80 weight %. In a further embodiment, the amount range of the glucokinase activator is about 70 weight % to about 90 weight %. In a further embodiment, the amount range of the glucokinase activator is about 80 weight % to about 100 weight %.

The amount of polymer carriers used in the solid dispersion of the glucokinase activator may vary in the range from about 1 weight % to about 99 weight %, based on the total weight of the solid dispersion. In one embodiment, the range of content of the polymer carriers is about 1 weight %, about 2 weight %, about 3 weight %, about 4 weight %, about 5 weight %, about 6 weight %, about 7 weight %, about 8 weight %, about 9 weight %, about 10 weight %, about 11 weight %, about 12 weight %, about 13 weight %, about 14 weight %, about 15 weight %, about 16 weight %, about 17 weight %, about 18 weight %, about 19 weight %, about 20 weight %, about 21 weight %, about 22 weight %, about 23 weight %, about 24 weight %, about 25 weight %, about 26 weight %, about 27 weight %, about 28 weight %, about 29 weight %, about 30 weight %, about 31 weight %, about 32 weight %, about 33 weight %, about 34 weight %, about 35 weight %, about 36 weight %, about 37 weight %, about 38 weight %, about 39 weight %, about 40 weight %, about 41 weight %, about 42 weight %, about 43 weight %, about 44 weight %, about 45 weight %, about 46 weight %, about 47 weight %, about 48 weight %, about 49 weight %, about 50 weight %, about 51 weight %, about 52 weight %, about 53 weight %, about 54 weight %, about 55 weight %, about 56 weight %, about 57 weight %, about 58 weight %, about 59 weight %, about 60 weight %, about 61 weight %, about 62 weight %, about 63 weight %, about 64 weight %, about 65 weight %, about 66 weight %, about 67 weight %, about 68 weight %, about 69 weight %, about 70 weight %, about 71 weight %, about 72 weight %, about 73 weight %, about 74 weight %, about 75 weight %, about 76 weight %, about 77 weight %, about 78 weight %, about 79 weight %, about 80 weight %, about 81 weight %, about 82 weight %, about 83 weight %, about 84 weight %, about 85 weight %, about 86 weight %, about 87 weight %, about 88 weight %, about 89 weight %, about 90 weight %, about 91 weight %, about 92 weight %, about 93 weight %, about 94 weight %, about 95 weight %, about 96 weight %, about 97 weight %, about 98 weight %, or about 99 weight %, or any subrange thereof within it. In one embodiment of the disclosure, the range of content of polymer carriers is about 1 weight % to about 20 weight %. In a further embodiment, the the range of content may be about 2 weight % to about 40 weight %. In a further embodiment, the range of content is about 30 weight % to about 60 weight %. In a further embodiment, the range of content is about 60 weight % to about 80 weight %. In a further embodiment, the range of content is about 70 weight % to about 90 weight %. In a further embodiment, the range of content is about 80 weight % to about 100 weight %.

Preferably, in the solid dispersion of the glucokinase activator of the present disclosure, the range of content of the glucokinase activator is 30-60 weight %, and that of polymer carriers is 40-70 weight %, on the basis of the total weight of the solid dispersion.

More preferably, in the solid dispersion of the glucokinase activator of the present disclosure, the range of content of the glucokinase activator is 40-60 weight %, and that of polymer carriers is 40-60 weight %, on the basis of the total weight of solid dispersion.

In one embodiment of the disclosure, the polymer carriers in the solid dispersion are selected from the group consisting of a polypropylene resin-based polymer, which is a polymeric compound derived from the polymerization of acrylic acid (or methacrylic acid and esters thereof such as methyl ester, ethyl esters and the like) (a monomer), or derived from the polymerization of two monomers (binary polymerization) or three monomers (ternary polymerization) in a certain ratio using acrylic acid and methacrylic acid (or its ester such as methyl ester, ethyl ester, dimethylaminoethyl ester, etc.).

The polymer carriers used in the solid dispersion of the present disclosure are selected from the group consisting of copolymer of butyl methacrylate, dimethylaminoethyl methacrylate and methyl methacrylate; copolymer of methacrylic acid and ethyl acrylate; copolymer of methacrylic acid and methyl methacrylate; copolymer of ethyl acrylate, methyl methacrylate and chlorotrimethylamino ethyl methacrylate; copolymer of ethyl acrylate and methyl methacrylate; copolymer of methacrylic acid, methyl acrylate and methyl methacrylate, and copolymer of methacrylic acid and butyl acrylate.

Furthermore, the polymer carriers are selected from the group consisting of copolymer of butyl methacrylate, dimethylaminoethyl methacrylate and methyl methacrylate (1:2:1), copolymer of methacrylic acid and ethyl acrylate (1:1), copolymer of methacrylic acid and methyl methacrylate (1:2), copolymer of ethyl acrylate, methyl methacrylate and chlorotrimethylamino ethyl methacrylate (1:2:0.2), copolymer of ethyl acrylate, methyl methacrylate and chlorotrimethylamino ethyl methacrylate (1:2:0.1), copolymer of ethyl acrylate and methyl methacrylate (2:1), copolymer of methacrylic acid and butyl acrylate (35:65), copolymer of methacrylic acid and methyl methacrylate (1:1), copolymer of methacrylic acid and methyl methacrylate (35:65).

Furthermore, the polymer carrier is Eudragit, including Eudragit E, Eudragit L, Eudragit S, Eudragit RL and Eudragit RS, wherein Eudragit E is produced by the polymerization of dimethylamino methacrylate and other neutral methacryates, including copolymers of dimethylaminoethyl methacrylate and methacrylate; Eudragit L and Eudragit S is produced by the polymerization of methacrylic acid and methacrylates in various ratios, including methacrylic acid and methyl methacrylate, free carboxyl:ester=1:1 or methacrylic acid and methyl methacrylate, free carboxyl:ester=1:2; Eudragit RL and Eudragit RS type is a copolymer of acrylic acid containing some quaternary amine groups and methacrylate, including the copolymer of acrylic acid containing 10% quaternary amine group and methacrylate and the copolymer of acrylic acid containing 5% quaternary amine group and methacrylate.

Furthermore, the polymer carriers is selected from the group consisting of:

Eudragit E100, which is copolymer of butyl methacrylate, dimethylaminoethyl methacrylate and methyl methacrylate (1:2:1), including Eudragit E PO;

Eudragit L100, methacrylic acid copolymer A TYPE, which is anion copolymer of methacrylic acid and methyl methacrylate (1:1);

Eudragit S 100, which is copolymer of methacrylic acid and methyl methacrylate (1:2);

Also, it can be appreciated that the examples of additional excipients used in the solid dispersion composition and formulation of the glucokinase activator of the present disclosure include but not limiting to diluent such as diluent for tablet and/or capsule; sweetener or flavoring agent; antioxidant; surfactant; filler; binder; disintegrant such as disintegrant for tablet; lubricant such as lubricant for tablet and/or capsule; glidant/antiadherent; release modifier; stabilizer; coating agents; colorant; chelating agent; emulsifier and/or solubilizer; flavoring agent and perfume.

Examples of diluents that suitable for the use in the disclosure include but not limiting to omega-3 fatty acids or derivatives thereof, lactose, dextrose, sucrose, mannitol, sorbitol, cellulose including silicified microcrystalline cellulose, sodium saccharin, glucose and/or glycine. Furthermore, in addition to those listed above, the tablet and/or capsule diluent that are suitable in the disclosure include but not limiting calcium carbonate, calcium hydrogen phosphate, calcium phosphate, calcium sulfate, cellulose powder, glucan binding agent, fructose, kaolin, starch, pregelatinized starch, compressible sugar and confectionery sugar and combinations thereof.

Examples of sweeteners or flavoring agents that are suitable for the disclosure include, but are not limited to, essential oils, water soluble extracts, sugar, monosaccharides, oligosaccharides, aldose, ketose, dextrose, maltose, lactose, glucose, fructose, sucrose, mannitol xylitol, D-sorbitol, erythritol, pentitol, hexitol, maltitol, acesulfame potassium, talin, glycyrrhizin, sucralose, aspartame, saccharin, sodium saccharin, sodium cyclamate, eugenyl formate aldehyde flavorings and combinations thereof.

Examples of antioxidants that are suitable for the disclosure include, but are not limited to, α-tocopherol, ascorbic acid, ascorbyl palmitate, butylated hydroxyanisole, butylated hydroxytoluene, thioglycerol, potassium metabisulfite, propionic acid, propyl gallate, sodium ascorbate, sodium bisulfite, sodium metabisulfite and sodium sulfite and combinations thereof.

Examples of surfactants that are suitable for the disclosure include, but are not limited to a salt of an alkyl sulfate, such as a lauryl sulfate diethanol ammonium salt; an alkyl aryl sulfonate such as calcium dodecylbenzenesulfonate; an alkylphenol-oxyalkylene addition product such as nonylphenol-C18 ethoxylate; alcohol-alkylene oxide addition product, such as tridecyl alcohol-C16 ethoxylate; soap, such as sodium stearate; alkylnaphthalene-sulfonate, such as dibutyl naphthalene sodium; a dialkyl ester of a sulfosuccinate such as sodium bis(2-ethylhexyl)sulfosuccinate; a sorbitol ester such as sorbitol oleate; a quaternary ammonium such as lauryl methyl-ammonium chloride; a polyethylene glycol ester of a fatty acid, such as polyethylene glycol stearate; a block copolymer of ethylene oxide and propylene oxide; a salt of a monoalkyl phosphate and a salt of a dialkyl phosphate; a vegetable oil, Such as soybean oil, rapeseed oil, olive oil, castor oil, sunflower oil, coconut oil, corn oil, cottonseed oil, linseed oil, palm oil, peanut oil, safflower oil, sesame oil, tung oil, etc.; and the ester of the above vegetable oil and the combination of them.

Examples of fillers that are suitable for the disclosure include, but are not limited to, cellulose derivatives such as microcrystalline cellulose or lignocellulose (including microcrystalline cellulose and silicified microcrystalline cellulose), lactose, anhydrous lactose or lactose monohydrate, sucrose, starch, pregelatinized starch, dextrose, mannitol (including mannitol Pearlitol SD 200), fructose, xylitol, sorbitol, corn starch, modified corn starch, inorganic salts such as calcium carbonate, calcium phosphate, dicalcium phosphate, calcium sulfate, dextrin/glucose binder, maltodextrin, compressible sugar and other known compatibilizers or fillers/or mixtures of two or more of them.

Examples of binders that are suitable for the disclosure include, but are not limited to, carboxymethylcellulose (including sodium carboxymethylcellulose), hydroxypropyl cellulose (including hydroxypropyl cellulose EXF), corn starch, pregelatinized starch, modified corn starch, polyvinyl pyrrolidone (PVP), hydroxypropylmethyl cellulose (HPMC) (including hydroxypropylmethyl cellulose 2208), lactose, gum arabic, ethylcellulose, cellulose acetate and wax binders such as carnauba wax, paraffin wax, cetyl wax, polyethylene or microcrystalline wax and other conventional binder and/or mixtures of two or more of them. Further, in addition to the above binders, tablet binders suitable for use in the present disclosure include, but are not limited to, alginic acid, microcrystalline cellulose, dextrin, gelatin, liquid glucose, guar gum, methylcellulose, polyethylene oxide, povidone and syrup, and the combination of them.

Examples of disintegrants that are suitable for the disclosure include, but are not limited to, croscarmellose sodium, crospovidone, starch, potato starch, pregelatinized starch, corn starch, sodium carboxymethyl starch, sodium starch glycolate, microcrystalline cellulose, low substituted hydroxypropyl cellulose and other known disintegrants. Several specific types of disintegrants are suitable for use in the formulations described herein. For example, any grade of crospovidone can be used including, for example, crospovidone XL-10 and selected from Kollidon CL®, Polyplasdone XL®, Kollidon CL-M®, Polyplasdone XL-10® and Polyplasdone INF-10®. Further, in addition to the above disintegrants, the disintegrant suitable for use in the tablet of the present disclosure includes, but is not limited to, alginic acid, polakolin potassium, sodium starch glycolate and pregelatinized starch and combinations thereof.

Examples of lubricants that are suitable for the disclosure include, but are not limited to, magnesium stearate, zinc stearate, calcium stearate, talc, carnauba wax, stearic acid, palmitic acid, sodium stearyl fumarate, sodium lauryl sulfate, glyceryl palmitostearate, palmitic acid, myristic acid and hydrogenation vegetable oil and fat and other known lubricant and/or mixtures of two or more of them. Further, in addition to the above-mentioned lubricants, the lubricants suitable for use in the tablet and/or capsule of the present disclosure includes, but is not limited to, glyceryl behenate, light mineral oil, polyethylene glycol, hard-purified stearic acid, and combinations thereof.

Examples of glidants and/or antiadherents that are suitable for the disclosure include, but are not limited to, silica, colloidal silica, magnesium silicate, magnesium trisilicate, talc and other forms of silica such as aggregated silicate and hydrated silica.

Examples of release modifiers that are suitable for the disclosure include, but are not limited to, hydroxypropylmethyl cellulose, polyvinyl alcohol (PVA), ethylcellulose, methacrylic acid(ester) polymer, hydroxypropyl cellulose, starch, gum, cellulose ether, protein-derived material, nylon, acrylic resin, polylactic acid, polyvinyl chloride, polyvinyl pyrrolidone and cellulose acetate phthalate and the combination thereof.

Stabilizers that are suitable for the present disclosure include, but are not limited to, fatty acids such as oleic acid and its sodium salt, cholic acid and deoxycholic acid, cationic lipids such as stearamide, and anionic stabilizers such as phosphatidylethanolamine, phosphatidylserine, phospholipids acid and phosphatidyl glycerols and the combinations thereof. In one embodiment, the stabilizer is oleic acid.

Coating agents that are suitable for the present disclosure include, but are not limited to, sodium carboxymethylcellulose, cellulose acetate, cellulose acetate phthalate, ethylcellulose, gelatin, pharmaceutical glaze, hydroxypropyl cellulose, hydroxypropylmethyl cellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcystalline wax, zein and Opadry such as Opadry 03K12429 and the combinations thereof.

Colorants that are suitable for the present disclosure include, but are not limited to, caramel, red colorant, yellow colorant, black colorant or blends thereof, ferric oxide and the combinations thereof.

Chelating agents that are suitable for the present disclosure include, but are not limited to, ethylenediamine tetraacetic acid and salts (EDTA), edetic acid, gentisic acid ethanolamide, oxyquinoline sulfate and the combinations thereof.

Emulsifiers and/or solubilizers that are suitable for the present disclosure include, but are not limited to, acacia, cholesterol, diethanolamine, glyceryl monostearate, lanolin alcohols, lecithin, mono- and di-glycerides, monoethanolamine, oleic acid, oleyl alcohol, poloxamer, polyoxyethylene 50 stearate, polyoxyethylene 35 caster oil, polyoxyethylene 40 hydrogenated castor oil, polyoxyl 10 oleyl ether, polyoxyethylene 20 cetostearyl ether, polyoxyethylene 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, triethanolamine, emulsifying wax and the combinations thereof.

Flavoring agents and perfumes that are suitable for the present disclosure include, but are not limited to, anethiol, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin and the combination thereof.

Solvents suitable for use in the present disclosure include, but are not limited to, acetone, alcohol, anhydrous ethanol, dilute alcohol, pentene hydrate, benzyl benzoate, butanol, carbon tetrachloride, chloroform, corn oil, cottonseed oil, ethyl acetate, glycerin, hexanediol, isopropanol, methanol, dichloromethane, methyl isobutyl ketone, mineral oil, peanut oil, polyethylene glycol, propylene carbonate, propylene glycol, sesame oil, water for injection, sterile water for injection, sterile rinse water, pure water and the combination thereof.

The amount of the active compound in a unit dosage formulation may vary or change from about 1 mg to about 200 mg, or preferably from about 2 mg to about 150 mg, more preferably from about 2.5 mg to about 150 mg, and more preferably from about 5 mg to about 150 mg, depending on the particular application.

Specifically, the content of the glucokinase activator in a unit tablet of the present disclosure is from about 1 mg to about 200 mg, preferably from about 2 mg to about 150 mg, and more preferably from about 5 mg to about 100 mg.

The invention will be further described with reference to the accompanying drawings and specific embodiments, but the invention is not limited to the embodiments, and various modifications and substitutions made on the basis of the technology of the invention are within the scope of the invention.

EXAMPLES

Preparation of the Solid Dispersion of the Glucokinase Activator

The chemical agents used in the disclosure were commercially available from companies including Shin-Etsu Japan, Evonik Germany, J.T. Baker US, SCR China, Ashland US, FMC US, JRS Germany, Colorcon US, Capsugel, BASF, Zhenxing China, and the like. Production equipments and analytical test equipments and the like were commercially available from such companies as Sartorius, Nikon, Sympatec, Bruker, Gea Niro, Korsch, Erweka, Agilent, Quadro Engineering, Canada; Warters, US; TA, US; SOTAX, Switzerland; Mettler Toledo Instrument Newark, Del., I. Preparation of Solid Dispersion of the Glucokinase Activator 1.1 Preparation of the Solution of the Solid Dispersion Used for Spray Drying Example 1 Weight Ratio of Active Ingredients to Polymer Carriers is 1:9)

6.75 g Eudragit L100 (Evonik Germany) was weighed, and added to anhydrous ethanol (J.T. Baker) under stirring. After it was completely dissolved, 0.75 g of the compound HMS5552 was added. Stirring was continued after adding sufficient amount of anhydrous ethanol to obtain 50 ml solution in a yellow to orange color.

Example 2 Weight Ratio of Active Ingredients to Polymer Carriers is 3:7

5.25 g Eudragit L100 (Evonik Germany) was weighed, and added to anhydrous ethanol (J.T. Baker) under stirring. After it was completely dissolved, 2.25 g of the compound HMS5552 was added. Stirring was continued after adding sufficient amount of anhydrous ethanol to obtain 50 ml solution in a yellow to orange color.

Example 3 Weight Ratio of Active Ingredients to Polymer Carriers is 5:5

3.75 g Eudragit L100 (Evonik Germany) was weighed, and added to anhydrous ethanol (J.T. Baker) under stirring. After it was completely dissolved, 3.75 g of the compound HMS5552 was added. Stirring was continued after adding sufficient amount of anhydrous ethanol to obtain 50 ml solution in a yellow to orange color.

Example 4 Weight Ratio of Active Ingredients to Polymer Carriers is 7:3

2.25 g Eudragit L100 (Evonik Germany) was weighed, and added to anhydrous ethanol (J.T. Baker) under stirring. After it was completely dissolved, 5.25 g of the compound HMS5552 was added. Stirring was continued after adding sufficient amount of anhydrous ethanol to obtain 50 ml solution in a yellow to orange color.

Example 5 Weight Ratio of Active Ingredients to Polymer Carriers is 8:2

1.5 g Eudragit L100 (Evonik Germany) was weighed, and added to anhydrous ethanol (J.T. Baker) under stirring. After it was completely dissolved, 6 g of the compound HMS5552 was added. Stirring was continued after adding sufficient amount of anhydrous ethanol to obtain 50 ml solution in a yellow to orange color.

Example 6 Weight Ratio of Active Ingredients to Polymer Carriers is 9:1

0.75 g Eudragit L100 (Evonik Germany) was weighed, and added to anhydrous ethanol (J.T. Baker) under stirring. After it was completely dissolved, 6.75 g of the compound HMS5552 was added. Stirring was continued after adding sufficient amount of anhydrous ethanol to obtain 50 ml solution in a yellow to orange color.

Example 7 Weight Ratio of Active Ingredients to Polymer Carriers is 6:4

3.0 g Eudragit L100 (Evonik Germany) was weighed, and added to anhydrous ethanol (J.T. Baker) under stirring. After it was completely dissolved, 4.5 g of the compound HMS5552 was added. Stirring was continued after adding sufficient amount of anhydrous ethanol to obtain 50 ml solution in a yellow to orange color.

Example 8 Weight Ratio of Active Ingredients to Polymer Carriers is 4:6

4.5 g Eudragit L100 (Evonik Germany) was weighed, and added to anhydrous ethanol (J.T. Baker) under stirring. After it was completely dissolved, 3.0 g of the compound HMS5552 was added. Stirring was continued after adding sufficient amount of anhydrous ethanol to obtain 50 ml solution in a yellow to orange color.

Example 9 Weight Ratio of Active Ingredients to Polymer Carriers is 5:5

187.5 g Eudragit L100 (Evonik Germany) was weighed, and added to anhydrous ethanol (Zhenxing China). After it was completely dissolved, 187.5 g of the compound HMS5552 was added. Stirring was continued after adding sufficient amount of anhydrous ethanol to obtain 2500 ml solution in a yellow to orange color.

1.2 Preparation of the Solid Dispersion of the Glucokinase Activator

The solid dispersion of the glucokinase activator was prepared by spray drying the solution prepared above. The numbering of the obtained solid dispersion corresponds to the numbering of the above examples. The spray drying devices that are suitable for the present disclosure include, but are not limited to, the spray drying devices produced by Niro GEA Process Engineering Inc., Buchi Labortechnik AG, ProCept and SPX ANHYDROUS companies. The Spray drying can be performed by selecting an appropriate inlet air temperature of dry gas, inlet amount, feed rate, and atomization pressure, so that the droplets are sufficiently dried as they reach the device wall. This can make sure that the dried droplets are essentially solid and in a form a fine powder, which will not stick to the wall, and is not difficult to collect in the cyclone. The resulting powder is subjected to a secondary drying to make sure the product meets quality requirement.

Description of the Production Process for the Preparation of the Solid Dispersion of the Glucokinase Activator by Spray Drying The solid dispersions were prepared by the spray drying the solution prepared in the above Examples 1-8, wherein the inlet air temperature of the spray dryer was 90-150° C., the flow rate of the inlet air was 0.3-0.5 m³/min, the flow rate of the air flow was 15-30 L/min, and the spray rate of above solutions were 5-7 mL/min. Solid dispersions 1-8 were obtained by spray drying.

The solid dispersion was prepared by spray drying the solution prepared in the above Example 9, wherein the inlet air temperature of the spray dryer was 90-150° C., the flow rate of the inlet air was 20-30 kg/h, the flow rate of the air flow was 3-30 kg/h, and the spray rate of above solutions were 5-200 mL/min. Solid dispersion 9 was obtained by spray drying.

Solid dispersions 1-9 were prepared according to the process described above, wherein:

Mass percent of the compound HMS5552 in solid dispersion 1 was 10%; mass percent of the compound HMS5552 in solid dispersion 2 was 30%; mass percent of the compound HMS5552 in solid dispersion 3 was 50%; mass percent of the compound HMS5552 in solid dispersion 4 was 70%; mass percent of the compound HMS5552 in solid dispersion 5 was 80%; mass percent of the compound HMS5552 in solid dispersion 6 was 90%; mass percent of the compound HMS5552 in solid dispersion 7 was 60%; mass percent of the compound HMS5552 in solid dispersion 8 was 40%; and mass percent of the compound HMS5552 in solid dispersion 9 was 50%.

II. Preparation of Tablets of the Glucokinase Activator

The coated tablets may be prepared using the formulation as described in the captioned "Preparation of tablets of the glucokinase activator", or a separate formulation. The coating film mainly functions to increase the hardness, facilitate moisture resistance, increase the aesthetic appearance, facilitate swallowing, and the like. Preparation steps of coated tablet of the glucokinase activator comprises:

(1) Preparing tablets of the glucokinase activator, wherein, the formulation and the preparation process were as described above.

(2) Preparing the coating solution: a coating suspension with a solid content of 15 weight % was prepared under stirring and was stirred uniformly.

(3) Coating: the core of the tablet was weighed into a coating pan. After the temperature of the coating bed reached 30-60° C., the coating started. The weight gain of the target coating is 2 weight % to 4 weight %, and the spraying of the coating solution was stopped after achieving the desired weight gain. After the coating bed was cooled to 25-30° C. tablets were released.

The following coated tablets of the glucokinase activator with the following doses were prepared according to this method. The formulations of these coated tablets are listed below.

Example 10 Formulation of 5 mg Tablet (Based on 1000 Tablets), i.e., the Amount of the Active Ingredient is 5 mg

| composition of formulation | unit formulation/g | % (w/w) |
| --- | --- | --- |
| solid dispersion 9 | 10.0 | 3.1 |
| silicified microcrystalline cellulose | 297.5 | 93.0 |
| hydroxypropyl cellulose | 7.5 | 2.3 |
| croscarmellose sodium | 2.5 | 0.78 |
| magnesium stearate | 2.5 | 0.78 |
| total | 320.0 | 100 |

Example 11 Formulation of 100 mg Tablet (Based on 1000 Tablets), i.e., the Amount of the Active Ingredient is 100 mg

| composition of formulation | unit formulation/g | % (w/w) |
| --- | --- | --- |
| solid dispersion 9 | 200.0 | 81.6 |
| silicified microcrystalline cellulose | 32.5 | 13.3 |

| composition of formulation | unit formulation/g | % (w/w) |
|---|---|---|
| hydroxypropyl cellulose | 7.5 | 3.1 |
| croscarmellose sodium | 2.5 | 1.02 |
| magnesium stearate | 2.5 | 1.02 |
| total | 245.0 | 100 |

Example 12 Formulation of 25 mg Tablet (Based on 1000 Tablets), i.e., the Amount of the Active Ingredient is 25 mg

| composition of formulation | unit formulation/g | % (w/w) |
|---|---|---|
| solid dispersion 9 | 50.0 | 15.6 |
| silicified microcrystalline cellulose | 257.5 | 80.5 |
| hydroxypropyl cellulose | 7.5 | 2.3 |
| croscarmellose sodium | 2.5 | 0.78 |
| magnesium stearate | 2.5 | 0.78 |
| total | 320.0 | 100 |

Example 13 Formulation of 75 mg Tablet (Based on 1000 Tablets), i.e., the Amount of the Active Ingredient is 75 mg

| composition of formulation | unit formulation/g | % (w/w) |
|---|---|---|
| solid dispersion 9 | 150.0 | 54.5 |
| silicified microcrystalline cellulose | 112.5 | 40.9 |
| hydroxypropyl cellulose | 7.5 | 2.7 |
| croscarmellose sodium | 2.5 | 0.91 |
| magnesium stearate | 2.5 | 0.91 |
| total | 275.0 | 100 |

Example 14 Formulation of 25 mg Tablet (Based on 1000 Tablets), i.e., the Amount of the Active Ingredient is 25 mg

| composition of formulation | unit formulation/g | % (w/w) |
|---|---|---|
| solid dispersion 9 | 50.0 | 15.6 |
| silicified microcrystalline cellulose | 239.6 | 74.9 |
| hydroxypropylmethyl cellulose | 16.0 | 5.0 |
| sodium starch glycolate | 11.2 | 3.5 |
| magnesium stearate | 3.2 | 1.0 |
| total | 320.0 | 100 |

Example 15 Formulation of 50 mg Tablet (Based on 1000 Tablets), i.e., the Amount of the Active Ingredient is 50 mg

| composition of formulation | unit formulation/g | % (w/w) |
|---|---|---|
| solid dispersion 9 | 100.0 | 33.3 |
| microcrystalline cellulose | 183.5 | 61.2 |
| hydroxypropyl cellulose | 7.5 | 2.5 |
| croscarmellose sodium | 6.0 | 2.0 |
| magnesium stearate | 3.0 | 1.0 |
| total | 300.0 | 100 |

Example 16 Formulation of 100 mg Tablet (Based on 1000 Tablets), i.e., the Amount of the Active Ingredient is 100 mg

| composition of formulation | unit formulation/g | % (w/w) |
|---|---|---|
| solid dispersion 9 | 200.0 | 80.0 |
| lactose monohydrate | 27.5 | 11.0 |
| polyvinylpyrrolidone | 12.5 | 5.0 |
| croscarmellose sodium | 5.0 | 2.0 |
| Sodium stearyl fumarate | 5.0 | 2.0 |
| total | 250.0 | 100 |

III. Preparation of Coated Tablets of the Glucokinase Activator

The coated tablets may be prepared using the formulation as described in the captioned "Preparation of tablets of the glucokinase activator", or a separate formulation. The coating film mainly functions to increase the hardness, facilitate moisture resistance, increase the aesthetic appearance, facilitate swallowing, and the like. Preparation steps of coated tablet of the glucokinase activator comprises:

(1) Preparing tablets of the glucokinase activator, wherein, the formulation and the preparation process were as described above.

(2) Preparing the coating solution: a coating suspension having a solid content of 15 weight % was prepared under stirring and was stirred uniformly.

(3) Coating: the core of the tablet was weighed into a coating pan. After the temperature of the coating bed reached 30-60° C., the coating started. The weight gain of the target coating is 2 weight % to 4 weight %, and the spraying of the coating solution was stopped after achieving the desired weight gain. After the coating bed was cooled to 25-30° C. tablets were released.

The following coated tablets of the glucokinase activator with the following doses were prepared according to this method. The formulations of these coated tablets are listed below.

Example 17 Formulation of 50 mg Coated Tablet (Based on 1000 Tablets), i.e., the Amount of the Active Ingredient is 50 mg

| composition of formulation | unit formulation/g | % (w/w) |
|---|---|---|
| solid dispersion 9 | 100.0 | 33.3 |
| silicified microcrystalline cellulose | 187.5 | 62.5 |
| hydroxypropyl cellulose | 7.5 | 2.5 |

| composition of formulation | unit formulation/g | % (w/w) |
| --- | --- | --- |
| croscarmellose sodium | 2.5 | 0.83 |
| magnesium stearate | 2.5 | 0.83 |
| total | 300.0 | 100 |
| Opadry | 9.0 | 3.0 |

Example 18 Formulation of 75 mg Coated Tablet Formula (Based on 1000 Tablets), i.e., the Amount of the Active Ingredient is 75 mg

| composition of formulation | unit formulation/g | % (w/w) |
| --- | --- | --- |
| solid dispersion 9 | 150.0 | 54.5 |
| silicified microcrystalline cellulose | 112.5 | 40.9 |
| hydroxypropyl cellulose | 7.5 | 2.7 |
| croscarmellose sodium | 2.5 | 0.91 |
| magnesium stearate | 2.5 | 0.91 |
| total | 275.0 | 100 |
| Opadry | 8.25 | 3.0 |

IV. Preparation of Capsules of the Glucokinase Activator

Preparation Method 1 of Capsules:

(1) Weighing and sieving: the components in the formulation were weighed and sieved before use;

(2) Granulating: the intragranular microcrystalline cellulose, solid dispersion (solid dispersion 9 prepared above) and hydroxypropyl cellulose were placed in a wet granulator, premixing according to the preset parameters, and the weighed pure water was added for wet granulation. After discharge, the granules were wet granulated by a mill, dried to a LOD of 2-3 weight %, and then dry granulated by a mill.

(3) Capsule filling: Capsules were filled with granules. The capsule shell types suitable for use in the present disclosure are: gelatin capsules of animal origin, HPMC capsules of plant origin, enteric capsules, soft capsules, and the like.

Example 19 Formulation of 50 mg Capsule (Based on 1000 Capsules), i.e., the Amount of the Active Ingredient is 50 mg

| composition of formulation | unit formulation/g | % (w/w) |
| --- | --- | --- |
| solid dispersion 9 | 100.0 | 36.04 |
| silicified microcrystalline cellulose | 170.0 | 61.26 |
| hydroxypropyl cellulose | 7.5 | 2.70 |
| total | 277.5 | 100.0 |

Preparation Method 2 of Capsules:

(1) Weighing and sieving: the components in the formulation were weighed and sieved before use;

(2) Capsule filling: Capsules were directly filled with the mixed powders. The capsule shell types suitable for use in the present disclosure are: gelatin capsules of animal origin, HPMC capsules of plant origin, enteric capsules, and the like.

Example 20 Formulation of 50 mg Capsule (Based on 1000 Capsules), i.e., the Amount of the Active Ingredient is 50 mg

| composition of formulation | unit formulation/g | % (w/w) |
| --- | --- | --- |
| solid dispersion 9 | 100.0 | 33.33 |
| silicified microcrystalline cellulose | 192.5 | 64.17 |
| croscarmellose sodium | 7.5 | 2.50 |
| total | 300.0 | 100 |

Example 21 Formulation of 25 mg Capsule (Based on 1000 Capsules), i.e., the Amount of the Active Ingredient is 25 mg

| composition of formulation | unit formulation/g | % (w/w) |
| --- | --- | --- |
| solid dispersion 9 | 50 | 16.67 |
| silicified microcrystalline cellulose | 247.5 | 82.5 |
| croscarmellose sodium | 2.5 | 0.83 |
| total | 300.0 | 100 |

V. Comparative Examples

The comparative example 1 and comparative example 2 were prepared by replacing the solid dispersion 9 in Example 12 and Example 13 with the active pharmaceutical ingredient of the compound HMS5552, adjusting the amount of microcrystalline cellulose in the formulation, and keeping other components and their ratio unchanged, and using the above preparation process for the tablets of the glucokinase activator.

Comparative Example 1 Formulation of 25 mg Tablet (Based on 1000 Tablets), i.e., the Amount of the Active Ingredient is 25 mg

| composition of formulation | unit formulation/g | % (w/w) |
| --- | --- | --- |
| compound HMS5552: active pharmaceutical ingredient | 25 | 7.8 |
| silicified microcrystalline cellulose | 282.5 | 88.3 |
| hydroxypropyl cellulose | 7.5 | 2.3 |
| croscarmellose sodium | 2.5 | 0.78 |
| magnesium stearate | 2.5 | 0.78 |
| total | 320.0 | 100 |

Comparative Example 2 Formulation of 75 mg Tablet (Based on 1000 Tablets), i.e., the Amount of the Active Ingredient is 75 mg

| composition of formula | unit formulation/g | % (w/w) |
| --- | --- | --- |
| compound HMS5552: active pharmaceutical ingredient | 75.0 | 27.3 |
| silicified microcrystalline cellulose | 187.5 | 68.2 |
| hydroxypropyl cellulose | 7.5 | 2.7 |

-continued

| composition of formula | unit formulation/g | % (w/w) |
|---|---|---|
| croscarmellose sodium | 2.5 | 0.91 |
| magnesium stearate | 2.5 | 0.91 |
| total | 275.0 | 100 |

The comparative example 3 and comparative example 4 were prepared by replacing the solid dispersion 9 in Example 12 and Example 13 with active pharmaceutical ingredient of the compound HMS5552, and Eudragit L100, keeping other components and their ratio unchanged, and using the preparation process for the tablets of the glucokinase activator above.

Comparative Example 3 Formulation of 25 mg Tablet (Based on 1000 Tablets), i.e., the Amount of the Active Ingredient is 25 mg

| composition of formulation | unit formulation/g | % (w/w) |
|---|---|---|
| compound HMS5552: active pharmaceutical ingredient | 25.0 | 7.8 |
| Eudragit L100 | 25.0 | 7.8 |
| silicified microcrystalline cellulose | 257.5 | 80.5 |
| hydroxypropyl cellulose | 7.5 | 2.3 |
| croscarmellose sodium | 2.5 | 0.78 |
| magnesium stearate | 2.5 | 0.78 |
| total | 320.0 | 100 |

Comparative Example 4 Formulation of 75 mg Tablet (Based on 1000 Tablets), i.e., the Amount of the Active Ingredient is 75 mg

| composition of formulation | unit formulation/g | % (w/w) |
|---|---|---|
| compound HMS5552: active pharmaceutical ingredient | 75.0 | 27.3 |
| Eudragit L100 | 75.0 | 27.3 |
| silicified microcrystalline cellulose | 112.5 | 40.9 |
| hydroxypropyl cellulose | 7.5 | 2.7 |
| croscarmellose sodium | 2.5 | 0.91 |
| magnesium stearate | 2.5 | 0.91 |
| total | 275.0 | 100 |

Tablets of the glucokinase activator in other doses or strengths can be prepared in the same manner.

VI. Test

1. Pharmacokinetics of the Oral Formulation of the Glucokinase Activator in Human Body Tablets prepared in the Examples above or in the same manner as the above-described Examples were used. In the Single Ascending Dose (SAD) test, plasma concentrations of the active ingredient increased rapidly after administration of a single oral dose of 5 mg, 10 mg, 15 mg, 25 mg, 35 mg and 50 mg of the active ingredient in healthy subjects, with an average peak time of 1.25-2.5 hours, followed by a steady drop, and the terminal elimination half-life was about 4.5-7.5 hours.

Tablets prepared in the Examples above or in the same manner as the above-described Examples were used. In the Multiple Ascending Dose (MAD) test, plasma concentrations of the active ingredient increased rapidly after administration of a single oral dose of 25 mg, 50 mg, 100 mg, 150 mg, and 200 mg of the active ingredient to patients with type 2 diabetes (T2DM), with an average peak time of 1.5-2 hours, followed by a steady drop, and the terminal elimination half-life was about 6.8-8.6 hours, which had no significant difference from that of the healthy subjects; when orally administrated at 25 mg, 50 mg, 100 mg, 150 mg, 200 mg twice per day for 5.5 consecutive days to achieve a steady state, the average time to reach the peak plasma concentration was 1.5-3 hours, and the terminal elimination half-life was about 7.7-10.3 hours. The plasma exposure was basically no accumulation as compared with the single administration to T2DM patients (the accumulation ratio range is 1-1.8).

Figure 1:
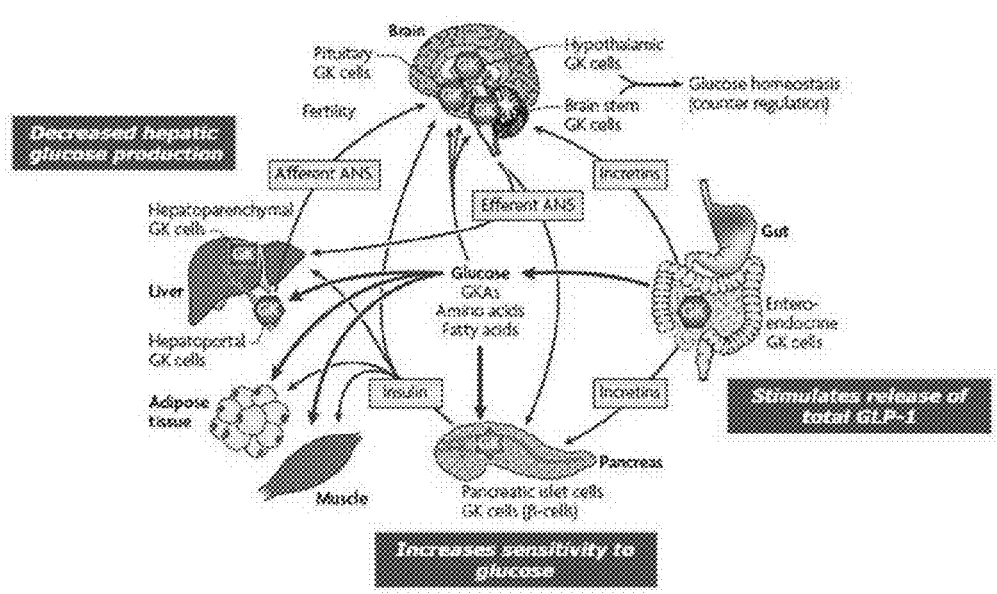
FIG. 1 is a graph which shows the distribution of the glucokinase in vivo.
Figure 2:
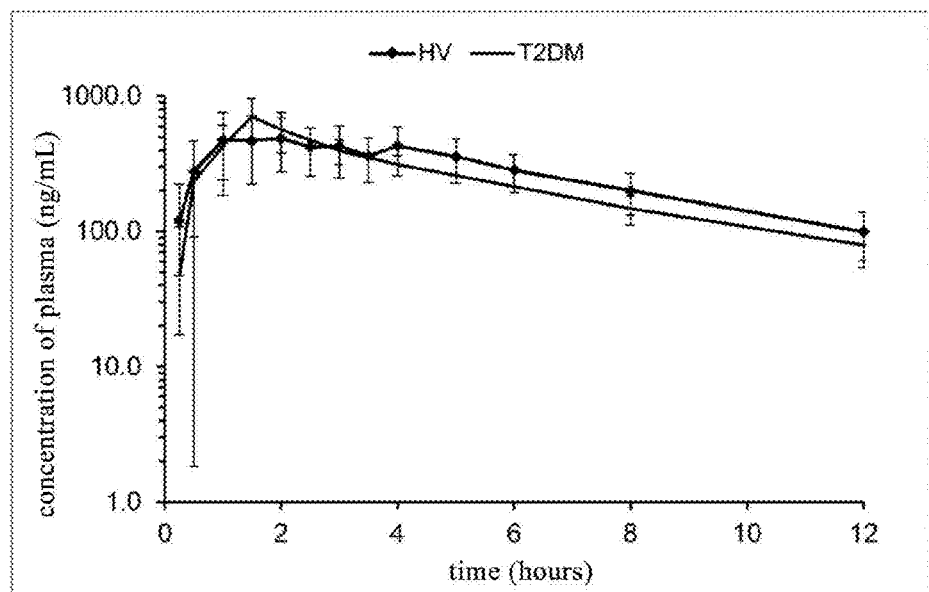
FIG. 2 is a graph which shows the plasma drug concentration versus time curve (semilog) of HMS5552 tablet in healthy subjects (HV) and patients with Type 2 diabetes (T2DM) after a single oral administration of 50 mg dosage.

After a single oral administration of tablets of the compound HMS5552 as prepared in Example 12 in a strength of 50 mg of the active ingredient, i.e., two tablets with 25 mg of the active ingredient, to healthy subjects (HV) and T2DM patients (T2DM), the plasma drug concentration after single oral administration versus time curve is shown in FIG. 2.

2. The Absorption of the Oral Formulation of the Glucokinase Activator in Human Intestinal Tract Simulated in PBPK Model The PBPK model was established by using Simcyp software to simulate the absorption degree and main absorption site of the compound HMS5552 in human intestinal tract after an oral administration of a single dose of 50 mg HMS5552 tablet in fasting healthy subjects.

Figure 3:
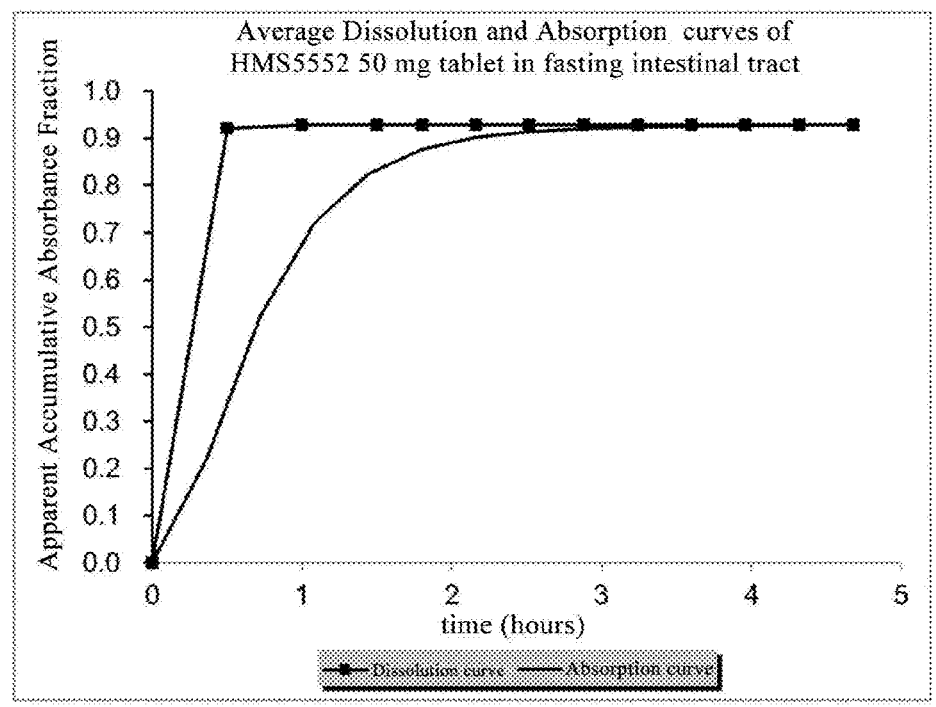
FIG. 3 is a graph which shows the simulated average dissolution and absorption profiles of HMS5552 50 mg tablet in fasting intestinal tract of human.

FIG. 3 is a graph showing the average dissolution rate and absorption profile of the oral formulation of the glucokinase activator in the intestine after a single dose of 50 mg oral formulation was administered to fasting healthy humans, simulated in the PBPK model. As seen from the figure, the oral formulation of the glucokinase activator is rapidly dissolved in the intestine, with a dissolution rate of 90% or higher in 30 minutes; as compared with the dissolution, the glucokinase activator was completely absorbed but in a slightly slow manner, reaching the absorption plateau in about 2-3 hours after administration. The result is in consistent with the clinically observed peak plasma time for the glucokinase activator in human, suggesting that the model can give a good prediction of the dissolution rate and absorption of the glucokinase activator in human body.

Figure 4:
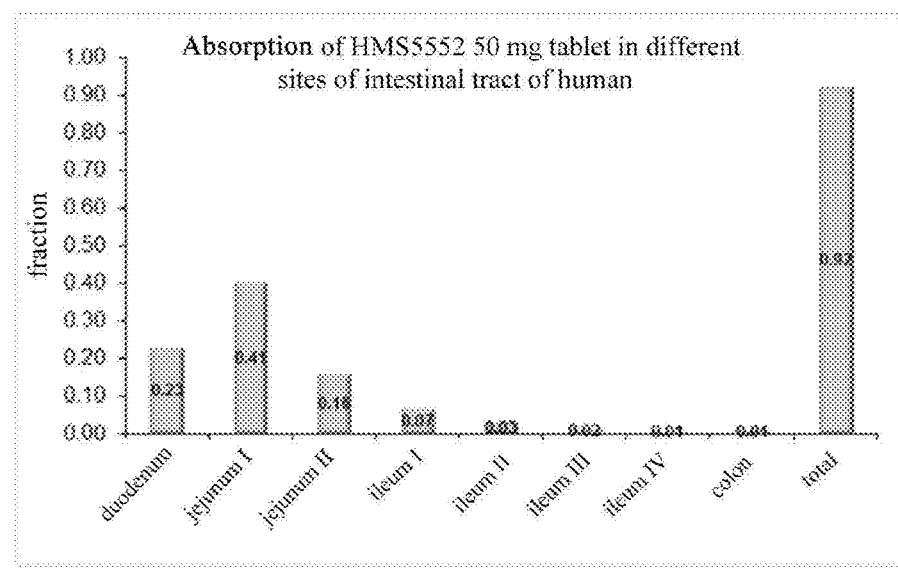
FIG. 4 is a graph which shows the simulated absorption distribution of HMS5552 50 mg tablet in different sites of fasting intestinal tract of human.

FIG. 4 shows the absorption fraction of the glucokinase activator in different parts of the human intestine when a single dose of 50 mg was administered to fasting healthy humans, simulated in the PBPK model. It can be observed that after a single administration of the HMS5552 tablet in human body, the main absorption site is located in duodenum of the anterior end of intestine, the segment I of the jejunum and the segment II of the jejunum. The total absorption fraction of the three parts is 0.8, accounting for 87% of the total absorption percent (0.92).

3. Dissolution Test In Vitro

The dissolution rate of the tablets and capsules were tested according the paddle method of the Chinese Pharmacopoeia (2010 edition), which was used to test the dissolution in three different dissolution medium at pH 1.2 and/or pH 4.5 and/or pH 6.8, respectively, at 5 minutes, 10 minutes, 20 minutes, 30 minutes, 45 minutes and 60 minutes. Each of 5 ml sample was taken for HPLC analysis.

The above tablets and capsules in five dosage strength were tested for their dissolution according to the above test, and the results were shown below.

TABLE 1

The dissolution rate of 25 mg tablet prepared in Example 12

| pH | \multicolumn{6}{c}{time point} | | | | | |
|---|---|---|---|---|---|---|
| | 5 | 10 | 20 | 30 | 45 | 60 |
| pH 6.8 | 57 | 83 | 92 | 95 | 96 | 97 |
| pH 4.5 | 8.7 | 13.7 | 18.6 | 21.6 | 24.8 | 27.3 |
| pH 1.2 | 8.4 | 12.8 | 16.6 | 18.7 | 20.6 | 22.0 |

TABLE 2

The dissolution rate of 5 mg tablet prepared in Example 10

| pH | time point | | | | | |
|---|---|---|---|---|---|---|
| | 5 | 10 | 20 | 30 | 45 | 60 |
| pH 6.8 | 57.8 | 81 | 91.1 | 94.1 | 95.9 | 96.7 |
| pH 4.5 | 17.1 | 25.1 | 32.4 | 36.8 | 41.6 | 45.3 |
| pH 1.2 | 13.4 | 18.4 | 22.1 | 24.0 | 25.9 | 27.3 |

TABLE 3

The dissolution rate of 50 mg coated tablet prepared in Example 17

| pH | time point | | | | | |
|---|---|---|---|---|---|---|
| | 5 | 10 | 20 | 30 | 45 | 60 |
| pH 6.8 | 51.3 | 73.4 | 85.6 | 92.1 | 97.2 | 99.8 |
| pH 4.5 | 8.2 | 11.7 | 15.7 | 18.1 | 20.8 | 22.8 |
| pH 1.2 | 7.1 | 9.8 | 12.7 | 14.5 | 16.1 | 17.2 |

TABLE 4

The dissolution rate of 75 mg coated tablet prepared in Example 18

| pH | time point | | | | | |
|---|---|---|---|---|---|---|
| | 5 | 10 | 20 | 30 | 45 | 60 |
| pH 6.8 | 96.9 | 100 | 100.1 | 100.8 | 101.0 | 101.0 |
| pH 4.5 | 10.0 | 15.7 | 20.3 | 23.6 | 26.8 | 28.9 |
| pH 1.2 | 8.1 | 11.7 | 14.7 | 16.5 | 18.0 | 19.1 |

TABLE 5

The dissolution rate of 100 mg tablet prepared in Example 11

| pH | time point | | | | | |
|---|---|---|---|---|---|---|
| | 5 | 10 | 20 | 30 | 45 | 60 |
| pH 6.8 | 60 | 85.2 | 95.2 | 99.3 | 100.7 | 101.2 |
| pH 4.5 | 6.0 | 9.5 | 14.1 | 17.2 | 20.5 | 23.8 |
| pH 1.2 | 4.9 | 7.6 | 10.6 | 12.3 | 14.4 | 15.8 |

TABLE 6

The dissolution rate of 25 mg capsule prepared in Example 21

| pH | time point | | | | | |
|---|---|---|---|---|---|---|
| | 5 | 10 | 20 | 30 | 45 | 60 |
| pH 6.8 | 65.83 | 89.35 | 95.24 | 95.97 | 96.89 | 97.64 |
| pH 4.5 | 25.9 | 37.24 | 40.6 | 43.96 | 46.38 | 47.65 |
| pH 1.2 | 31.8 | 36.43 | 39.37 | 40.69 | 42.81 | 44.29 |

TABLE 7

The dissolution rate of 75 mg tablet prepared in Example 13

| pH | time point | | | | | |
|---|---|---|---|---|---|---|
| | 5 | 10 | 20 | 30 | 45 | 60 |
| pH 6.8 | 64.5 | 79.7 | 86.3 | 88.6 | 90.8 | 92.0 |
| pH 4.5 | 13.4 | 16.9 | 21.5 | 24.6 | 28.4 | 31.3 |
| pH 1.2 | 8.4 | 11.5 | 14.3 | 16.2 | 18.1 | 19.4 |

TABLE 8

The dissolution rate of 25 mg tablet prepared in Example 14

| pH | time point | | | | | |
|---|---|---|---|---|---|---|
| | 5 | 10 | 20 | 30 | 45 | 60 |
| pH 6.8 | 41.7 | 71.6 | 88.9 | 95.8 | 99.3 | 103.1 |
| pH 4.5 | 18.7 | 24.0 | 29.1 | 33.2 | 38.1 | 41.6 |
| pH 1.2 | 9.1 | 13.4 | 17.6 | 20.1 | 22.3 | 23.5 |

TABLE 9

The dissolution rate of 50 mg tablet prepared in Example 15

| pH | time point | | | | | |
|---|---|---|---|---|---|---|
| | 5 | 10 | 20 | 30 | 45 | 60 |
| pH 6.8 | 81.3 | 92.4 | 95.1 | 95.8 | 96.1 | 96.3 |
| pH 4.5 | 16.6 | 22.9 | 29.1 | 32.9 | 36.9 | 40.0 |
| pH 1.2 | 14.4 | 19.3 | 22.6 | 24.7 | 26.7 | 27.9 |

TABLE 10

The dissolution rate of 100 mg tablet prepared in Example 16

| pH | time point | | | | | |
|---|---|---|---|---|---|---|
| | 5 | 10 | 20 | 30 | 45 | 60 |
| pH 6.8 | 49.4 | 74.7 | 88.7 | 93.6 | 96.4 | 97.3 |
| pH 4.5 | 7.9 | 12.8 | 18.3 | 21.9 | 25.8 | 28.3 |
| pH 1.2 | 1.5 | 3.3 | 8.1 | 11.3 | 14.9 | 16.8 |

TABLE 11

The dissolution rate of 25 mg tablet prepared in comparative example 1

| | time point | | | | | |
|---|---|---|---|---|---|---|
| pH | 5 | 10 | 20 | 30 | 45 | 60 |
| pH 6.8 | 43.1 | 61.9 | 83.2 | 91.4 | 97.4 | 99.9 |
| pH 4.5 | 38.5 | 57.5 | 77.8 | 84.7 | 92.9 | 96.8 |
| pH 1.2 | 41.3 | 60.9 | 79.8 | 87.9 | 94.0 | 97.1 |

TABLE 12

The dissolution rate of 75 mg tablet prepared in comparative example 2

| | time point | | | | | |
|---|---|---|---|---|---|---|
| pH | 5 | 10 | 20 | 30 | 45 | 60 |
| pH 6.8 | 25.6 | 40.8 | 56.9 | 65.3 | 73.6 | 79.8 |
| pH 4.5 | 24.4 | 40.7 | 57.8 | 67.2 | 76.3 | 82.0 |
| pH 1.2 | 36.5 | 46.9 | 58.9 | 68.5 | 80.2 | 85.7 |

TABLE 13

The dissolution rate of 25 mg tablet prepared in comparative example 3

| | time point | | | | | |
|---|---|---|---|---|---|---|
| pH | 5 | 10 | 20 | 30 | 45 | 60 |
| pH 6.8 | 53.3 | 73.9 | 89.9 | 95.4 | 98.6 | 99.3 |
| pH 4.5 | 50.9 | 68.4 | 84.7 | 91.1 | 95.0 | 96.3 |
| pH 1.2 | 43.8 | 66.0 | 83.9 | 91.1 | 95.4 | 97.5 |

TABLE 14

The dissolution rate of 75 mg tablet prepared in comparative example 4

| | time point | | | | | |
|---|---|---|---|---|---|---|
| pH | 5 | 10 | 20 | 30 | 45 | 60 |
| pH 6.8 | 24.7 | 40.4 | 58.6 | 68.7 | 78.7 | 85.2 |
| pH 4.5 | 30.9 | 41.7 | 58.8 | 68.1 | 77.0 | 82.6 |
| pH 1.2 | 30.6 | 46.6 | 62.5 | 72.3 | 80.9 | 85.8 |

CONCLUSION

Figure 5:
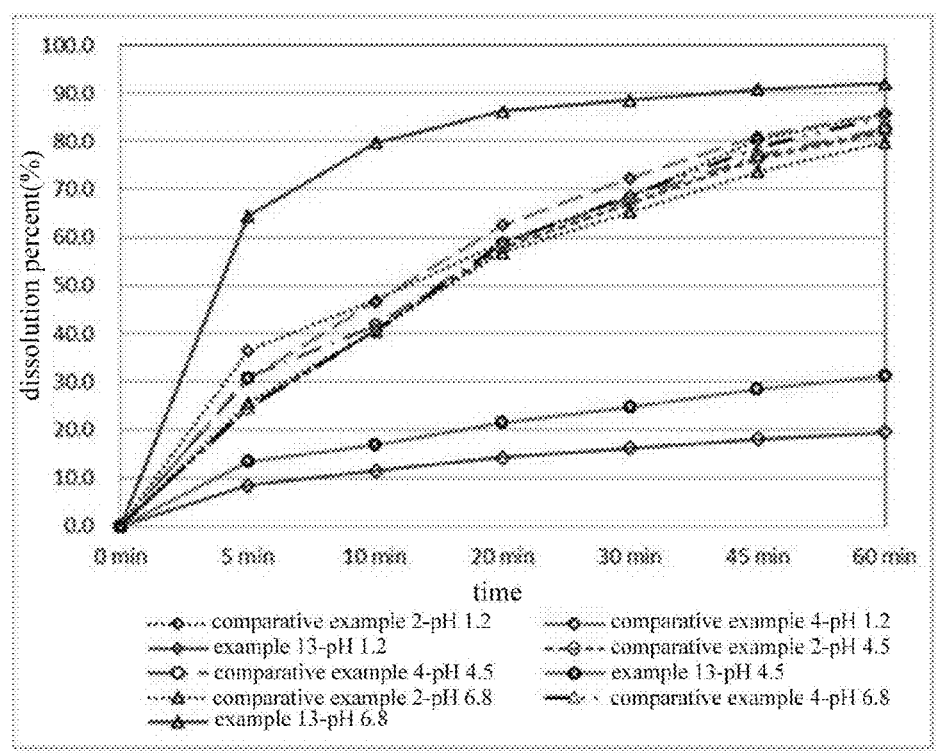
FIG. 5 is a graph which shows the dissolution curves of 75 mg tablets prepared in Example 13, comparative example 2 and comparative example 4 at pH 1.2, pH 4.5 and pH 6.8, respectively.
Figure 6:
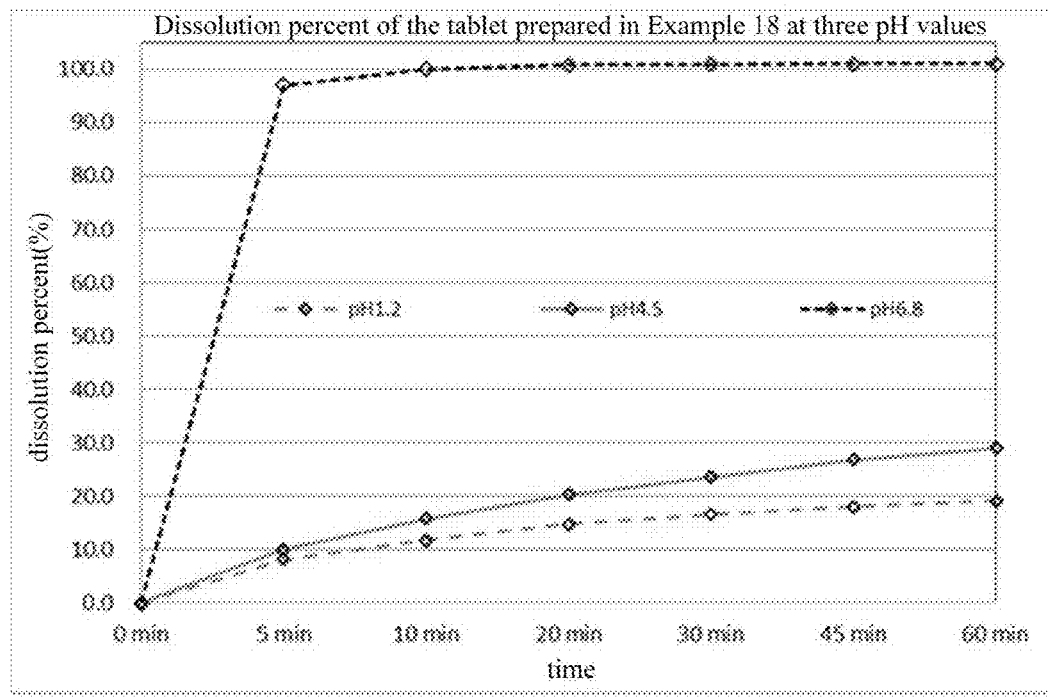
FIG. 6 is a graph which shows the dissolution curve of the 75 mg coated tablet prepared in Example 18 at pH 1.2, pH 4.5 and pH 6.8.

The oral formulations prepared by the solid dispersion technique of the present disclosure have significantly different dissolution rate at different pH; in contrast, the tablets prepared by the conventional processes do not exhibit this characteristic. As shown in FIG. 5, although the preparation process and the composition of the tablets are the same or similar, different forms of the compound HMS5552 result in different dissolution rate of the active ingredient HMS5552 in the oral formulation, i.e., pure HMS5552 powder (comparative example 2) or a simple mixture of HMS5552+Eudragit L100 (comparative example 4) or solid dispersion form (Example 13).

The above difference indicates that the dissolution of the tablet prepared by the solid dispersion technique of the present disclosure is pH-dependent. That is, the dissolution rate at 30 min is not higher than 45% at pH 1.2~4.5, and the dissolution rate at 30 min is not less than 85% at pH 6.0~7.0 (Tables 1-10).

Furthermore, as shown in FIGS. 7-9, the tablets prepared in the comparative example 2 and the comparative example 4 have similar dissolution rate at 30 min at pH 1.2, pH 4.5 and pH 6.8. While the tablet of Example 13 prepared by the solid dispersion technique of the present disclosure have dissolution rate at 30 min of 16.2%, 24.6%, and 88.6% at pH 1.2, pH 4.5, and pH 6.8, respectively.

The invention claimed is:

1. A solid dispersion, which comprises a glucokinase activator, or isotope labeled analogues thereof of pharmaceutically acceptable salts thereof, and a polymer carrier, wherein the glucokinase activator is the compound HMS5552, or isotope labeled analogues or pharmaceutically acceptable salts thereof,

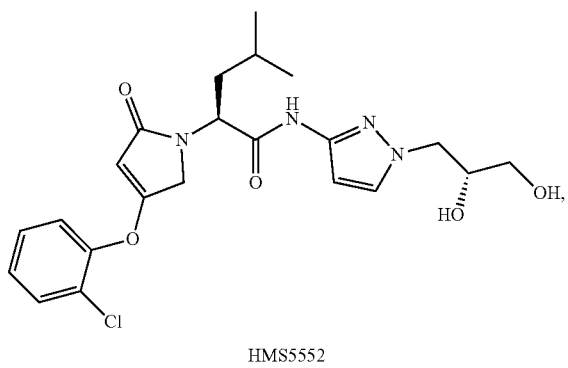 [SMILES: CC(C)C[C@@H](C(=O)Nc1ccn(C[C@@H](O)CO)n1)N1CC(Oc2ccccc2Cl)=CC1=O]

HMS5552 and wherein the polymer carrier is Eudragit L100.

2. The solid dispersion according to claim 1, wherein the weight ratio of the glucokinase activator to polymer carriers is 5:6 to 6:5.

3. The solid dispersion according to claim 1, wherein the weight ratio of the glucokinase activator to polymer carriers is 1:1.

4. A solid dispersion composition, which comprises the solid dispersion according to claim 1 and excipients.

5. A tablet of the glucokinase activator, wherein the tablet comprises the solid dispersion according to claim 1 and one or more selected from the group consisting of filler, binder, disintegrant and lubricant, wherein the content of the solid dispersion in the tablet is 1 weight % to 90 weight %, the content of filler is 1 weight % to 95 weight %, the content of binder is 0.5 weight % to 10 weight %, the content of disintegrant is 0.5 weight % to 7.5 weight %, and the content of lubricant is 0.25 weight % to 5 weight %, and wherein the amount of the glucokinase activator in the unit tablet is about 5 mg to about 200 mg.

6. The tablet according to claim 5, wherein the weight ratio of the glucokinase activator to the polymer carrier is 5:6 to 6:5, or 1:1.

7. The tablet of the glucokinase activator according to claim 6, which has a dissolution of <45% at pH1.2~4.5 at 30 min, and a dissolution of >85% at pH6.0~7.0 at 30 min.

8. The tablet of the glucokinase activator according to claim 5, wherein the tablet comprises 120 mg to 180 mg of the solid dispersion of the compound HMS5552, 33.1 mg to 151.6 mg silicified microcrystalline cellulose, 1.4 mg to 27.5 mg hydroxypropyl cellulose, 1.4 mg to 20.6 mg croscarmellose sodium and 0.7 mg to 13.8 mg magnesium stearate, wherein in the solid dispersion, the ratio of the compound HMS5552 to the polymer carrier is 1:1.

9. The tablet of the glucokinase activator according to claim 8, which comprises 150 mg of the solid dispersion of the compound HMS5552, 112.5 mg silicified microcrystalline cellulose, 7.5 mg hydroxypropyl cellulose, 2.5 mg croscarmellose sodium and 2.5 mg magnesium stearate, wherein the solid dispersion of the compound HMS5552 comprises 75 mg of the compound HMS5552.

10. The tablet of the glucokinase activator according to claim 5, wherein the tablet comprises 170 mg to 230 mg of the solid dispersion of the compound HMS5552, 2.5 mg to 71.9 mg silicified microcrystalline cellulose, 1.2 mg to 24.5 mg hydroxypropyl cellulose, 1.2 mg to 18.4 mg croscarmellose sodium and 0.6 mg to 12.3 mg magnesium stearate, wherein in the solid dispersion, the ratio of the compound HMS5552 to the polymer carrier is 1:1.

11. The tablet of the glucokinase activator according to claim 10, which comprises 200 mg of the solid dispersion of the compound HMS5552, 32.5 mg silicified microcrystalline cellulose, 7.5 mg hydroxypropyl cellulose, 2.5 mg croscarmellose sodium and 2.5 mg magnesium stearate, wherein the solid dispersion of the compound HMS5552 comprises 100 mg of the compound HMS5552.

12. The tablet of the glucokinase activator according to claim 5, wherein the tablet comprises 40 mg to 60 mg of the solid dispersion of the compound HMS5552, 188.0 mg to 276.0 mg silicified microcrystalline cellulose, 1.6 mg to 32.0 mg hydroxypropyl cellulose, 1.6 mg to 24.0 mg croscarmellose sodium and 0.8 mg to 16.0 mg magnesium stearate, wherein in the solid dispersion, the ratio of the compound HMS5552 to the polymer carrier is 1:1.

13. The tablet of the glucokinase activator according to claim 12, which comprises 50 mg of the solid dispersion of the compound HMS5552, 257.5 mg silicified microcrystalline cellulose, 7.5 mg hydroxypropyl cellulose, 2.5 mg croscarmellose sodium and 2.5 mg magnesium stearate, wherein the solid dispersion of the compound HMS5552 comprises 25 mg of the compound HMS5552.

14. The tablet of the glucokinase activator according to claim 5, wherein the tablet comprises 40 mg to 60 mg of the solid dispersion of the compound HMS5552, 188.0 mg to 276.0 mg silicified microcrystalline cellulose, 1.6 mg to 32.0 mg hydroxypropylmethyl cellulose, 1.6 mg to 24.0 mg sodium starch glycolate and 0.8 mg to 16.0 mg magnesium stearate, wherein in the solid dispersion, the ratio of the compound HMS5552 to the polymer carrier is 1:1.

15. The tablet of the glucokinase activator according to claim 14, wherein the tablet comprises 50 mg of the solid dispersion of the compound HMS5552, 239.6 mg silicified microcrystalline cellulose, 16.0 mg hydroxypropylmethyl cellulose, 11.2 mg sodium starch glycolate and 3.2 mg magnesium stearate, wherein the solid dispersion of the compound HMS5552 comprises 25 mg of the compound HMS5552.

16. The tablet of the glucokinase activator according to claim 5, wherein the tablet comprises 170 mg to 230 mg of the solid dispersion of the compound HMS5552, 2.5 mg to 71.9 mg lactose monohydrate, 1.2 mg to 24.5 mg polyvinylpyrrolidone, 1.2 mg to 18.4 mg croscarmellose sodium and 0.6 mg to 12.3 mg sodium stearyl fumarate, wherein in the solid dispersion, the ratio of the compound HMS5552 to the polymer carrier is 1:1.

17. The tablet of the glucokinase activator according to claim 16, wherein the tablet comprises 200 mg of the solid dispersion of the compound HMS5552, 27.5 mg lactose monohydrate, 12.5 mg polyvinylpyrrolidone, 5.0 mg croscarmellose sodium and 5.0 mg sodium stearyl fumarate, wherein the solid dispersion of the compound HMS5552 comprises 100 mg of the compound HMS5552.

18. The tablet of the glucokinase activator according to claim 5, wherein the tablet comprises 100 mg of the solid dispersion of the compound HMS5552, 183.5 mg microcrystalline cellulose, 7.5 mg hydroxypropyl cellulose, 6.0 mg croscarmellose sodium and 3.0 mg magnesium stearate, wherein the solid dispersion of the compound HMS5552 comprises 50 mg of the compound HMS5552.

19. The tablet of the glucokinase activator according to claim 5, which is coated tablet.

20. The coated tablet according to claim 19, wherein the weight ratio of the glucokinase activator to the polymer carrier is 5:6 to 6:5, or 1:1.

21. The tablet of the glucokinase activator according to claim 19, wherein the coated tablet comprises 80 mg to 120 mg of the solid dispersion of the compound HMS5552, 112.5 mg to 216.3 mg silicified microcrystalline cellulose, 1.5 mg to 30.0 mg hydroxypropyl cellulose, 1.5 mg to 22.5 mg croscarmellose sodium, 0.8 mg to 15.0 mg magnesium stearate and 3.0 mg to 30.0 mg Opadry, wherein in the solid dispersion, the ratio of the compound HMS5552 to the polymer carrier is 1:1.

22. The tablet of the glucokinase activator according to claim 21, which comprises 100 mg of the solid dispersion of the compound HMS5552, 187.5 mg silicified microcrystalline cellulose, 7.5 mg hydroxypropyl cellulose, 2.5 mg croscarmellose sodium, 2.5 mg magnesium stearate and 9 mg Opadry, wherein the solid dispersion of the compound HMS5552 comprises 50 mg of the compound HMS5552.

23. The tablet of the glucokinase activator according to claim 19, wherein the coated tablet comprises 120 mg to 180 mg of the solid dispersion of the compound HMS5552, 33.1 mg to 151.6 mg silicified microcrystalline cellulose, 1.4 mg to 27.5 mg hydroxypropyl cellulose, 1.4 mg to 20.6 mg croscarmellose sodium, 0.7 mg to 13.8 mg magnesium stearate and 2.75 mg to 27.5 mg Opadry, wherein in the solid dispersion, the ratio of the compound HMS5552 to the polymer carrier is 1:1.

24. The tablet of the glucokinase activator according to claim 23, which comprises 150 mg of the solid dispersion of the compound HMS5552, 112.5 mg silicified microcrystalline cellulose, 7.5 mg hydroxypropyl cellulose, 2.5 mg croscarmellose sodium, 2.5 mg magnesium stearate and 8.25 mg Opadry, wherein the solid dispersion of the compound HMS5552 comprises 75 mg of the compound HMS5552.

25. A capsule of the glucokinase activator, wherein the capsule comprises the solid dispersion of claim 1 and one or more materials selected from the group consisting of filler, binder, disintegrant and lubricant,
wherein the content of the solid dispersion is 1 weight % to 90 weight %, the content of filler is 5 weight % to 95 weight %, the content of binder is 0 weight % to 10 weight %, the content of disintegrant is 0.5 weight % to 7.5 weight %, and the content of lubricant is 0 weight % to 5 weight %, and
wherein in the unit formulation, the content of the glucokinase activator is about 5 mg to about 200 mg.

26. The capsule according to claim 25, wherein the weight ratio of the glucokinase activator to the polymer carrier is 5:6 to 6:5, or 1:1.

27. The capsule of the glucokinase activator according to claim 25, which has a dissolution of <45% at pH1.2~4.5 at 30 min, and a dissolution of >85% at pH6.0~7.0 at 30 min.

28. The capsule of the glucokinase activator according to claim 25, wherein the capsule comprises 80 mg to 120 mg of the solid dispersion of the compound HMS5552, 150.0 mg to 218.5 mg silicified microcrystalline cellulose, 1.5 mg to 22.5 mg croscarmellose sodium, wherein in the solid dispersion, the ratio of the compound HMS5552 to the polymer carrier is 1:1 wherein in the solid dispersion, the ratio of the compound HMS5552 to the polymer carrier is 1:1.

29. The capsule of the glucokinase activator according to claim 28, which comprises 100 mg of the solid dispersion of the compound HMS5552, 170 mg silicified microcrystalline cellulose, 7.5 mg hydroxypropyl cellulose, wherein the solid dispersion of the compound HMS5552 comprises 50 mg of the compound HMS5552.

30. The capsule of the glucokinase activator according to claim 25, wherein the capsule comprises 80 mg to 120 mg the solid dispersion of the compound HMS5552, 129.8 mg to 196.1 mg silicified microcrystalline cellulose, 1.4 mg to 27.8 mg hydroxypropyl cellulose, wherein in the solid dispersion, the ratio of the compound HMS5552 to the polymer carrier is 1:1 wherein in the solid dispersion, the ratio of the compound HMS5552 to the polymer carrier is 1:1.

31. The capsule of the glucokinase activator according to claim 28, wherein the capsule comprises 100 mg of the solid dispersion of the compound HMS5552, 192.5 mg silicified microcrystalline cellulose, 7.5 mg croscarmellose sodium, wherein the solid dispersion of the compound HMS5552 comprises 50 mg of the compound HMS5552.

32. The capsule of the glucokinase activator according to claim 25, wherein the capsule comprises 40 mg to 60 mg of the solid dispersion of the compound HMS5552, 217.5 mg to 258.5 mg silicified microcrystalline cellulose, 1.5 mg to 22.5 mg croscarmellose sodium, wherein in the solid dispersion, the ratio of the compound HMS5552 to the polymer carrier is 1:1.

33. The capsule of the glucokinase activator according to claim 32, which comprises 50 mg of the solid dispersion of the compound HMS5552, 247.5 mg silicified microcrystalline cellulose, 2.5 mg croscarmellose sodium, wherein the solid dispersion of the compound HMS5552 comprises 25 mg of the compound HMS5552.

34. The solid dispersion according to claim 1, wherein the weight ratio of the glucokinase activator to the polymer carrier is 1:4 to 4:1.

* * * * *

UNITED STATES PATENT AND TRADEMARK OFFICE
CERTIFICATE OF CORRECTION

| | | |
|---|---|---|
| PATENT NO. | : 11,266,630 B2 | Page 1 of 1 |
| APPLICATION NO. | : 16/470291 | |
| DATED | : March 8, 2022 | |
| INVENTOR(S) | : Li Chen et al. | |

It is certified that error appears in the above-identified patent and that said Letters Patent is hereby corrected as shown below:

In the Specification

Column 1, Line 16 should read: "The disclosure relates to the oral formulation of the"
Column 1, Line 26 should read: "The modified release of the oral formulation of the"
Column 3, Line 30 should read: "oral formulation of the glucokinase activator, in particular, an"
Column 4, Line 5 should read: "solid solution; glassy solution, and glassy suspension, etc."
Column 7, Lines 26-27 should read: "matography (chromatography with a chiral adsorbent or eluent). The disclosure embraces all of these forms."
Column 9, Line 10 should read: "to the design and preparation of the oral formulation of"
Column 17, Lines 31-32 should read: "tablet the fillers are silicified microcrystalline, cellulose, microcrystalline cellulose or lactose, the binders are hydroxy-"
Column 17, Lines 34-35 should read: "nyl pyrrolidone, the disintegrants are croscarmellose sodium or sodium carboxymethyl starch, and the lubricants are mag-"
Column 17, Line 55 should read: "microcrystalline wax, zein and Opadry."
Column 28, Line 36 should read: "sucrose, titanium dioxide, carnauba wax, microcrystalline"
Column 29, Line 53 should read: "oral formulation of the glucokinase activator in the"
Column 30, Line 47 should read: "coat the tablets, and then discharging the coated tablets."
Column 33, Line 33 should read: "weight %. In a further embodiment, the range of content"
Column 34, Line 36 should read: "Furthermore, the polymer carriers are selected from the"
Column 35, Line 58 should read: "ylene or microcrystalline wax and other conventional binder"
Column 36, Line 57 should read: "microcrystalline wax, zein and Opadry such as Opadry"
Column 37, Line 6 should read: "ylene 50 stearate, polyoxyethylene 35 castor oil, polyoxy-"
Column 37, Line 65 should read: "Quadro Engineering, Canada; Waters, US; TA, US;"
Column 39, Line 44 should read: "the dried droplets are essentially solid and in a form of a fine"
Column 43, Line 43 should read: "disclosure are as follows: gelatin capsules of animal origin, HPMC"
Column 43, Line 65 should read: "the present disclosure are as follows: gelatin capsules of animal origin,"
Column 44, Line 59 should read: "tested according to the paddle method of the Chinese Pharma-"

Signed and Sealed this
Eighth Day of November, 2022

Katherine Kelly Vidal
*Director of the United States Patent and Trademark Office*